United States Patent
Hatcher, Jr. et al.

(10) Patent No.: US 9,116,071 B2
(45) Date of Patent: Aug. 25, 2015

(54) SYSTEM AND METHOD FOR VISUAL INSPECTION AND 3D WHITE LIGHT SCANNING OF OFF-LINE INDUSTRIAL GAS TURBINES AND OTHER POWER GENERATION MACHINERY

(71) Applicants: Clifford Hatcher, Jr., Orlando, FL (US); Yakup Genc, Dayton, NJ (US); Richard Hatley, Morristown, NJ (US); Anton Schick, Veldon (DE)

(72) Inventors: Clifford Hatcher, Jr., Orlando, FL (US); Yakup Genc, Dayton, NJ (US); Richard Hatley, Morristown, NJ (US); Anton Schick, Veldon (DE)

(73) Assignee: Siemens Energy, Inc., Orlando, FL (US)

( * ) Notice: Subject to any disclaimer, the term of this patent is extended or adjusted under 35 U.S.C. 154(b) by 148 days.

(21) Appl. No.: 13/972,000

(22) Filed: Aug. 21, 2013

(65) Prior Publication Data
US 2013/0335530 A1    Dec. 19, 2013

Related U.S. Application Data

(63) Continuation-in-part of application No. 13/362,352, filed on Jan. 31, 2012, now Pat. No. 8,713,999, and a continuation-in-part of application No. 13/362,417, filed on Jan. 31, 2012, and a continuation-in-part of (Continued)

(51) Int. Cl.
| | |
|---|---|
| *G01M 15/14* | (2006.01) |
| *G01M 15/02* | (2006.01) |
| *F01D 21/00* | (2006.01) |
| *G01N 21/954* | (2006.01) |
| *G02B 23/24* | (2006.01) |

(52) U.S. Cl.
CPC ............. *G01M 15/02* (2013.01); *F01D 21/003* (2013.01); *G01N 21/954* (2013.01); *G02B 23/2484* (2013.01)

(58) Field of Classification Search
CPC ....................................... G01M 15/14
USPC ............... 73/112.01, 112.02, 112.03, 112.05, 73/118.03
See application file for complete search history.

(56) References Cited

U.S. PATENT DOCUMENTS

| | | |
|---|---|---|
| 5,102,221 A | 4/1992 | Desgranges et al. |
| 5,164,826 A | 11/1992 | Dailey |
| 5,349,850 A | 9/1994 | Young |

(Continued)

FOREIGN PATENT DOCUMENTS

EP    0907077    4/1999

OTHER PUBLICATIONS

Co-pending utility U.S. Appl. No. 13/971,938, filed Aug. 21, 2013.

(Continued)

*Primary Examiner* — Eric S McCall

(57) ABSTRACT

Internal components of gas or steam turbines are inspected with a 3D scanning camera inspection system that is inserted and positioned within the turbine, for example through a gas turbine combustor nozzle port. Three dimensional internal component measurements are performed using projected light patterns generated by a stripe projector and a 3D white light matrix camera. Real time dimensional information is gathered without physical contact, which is helpful for extracting off-line engineering information about the scanned structures. Exemplary 3D scans, preferably with additional visual images, are performed of the gas path side of a gas turbine combustor support housing, combustor basket and transition with or without human intervention.

20 Claims, 22 Drawing Sheets

Related U.S. Application Data application No. 13/362,387, filed on Jan. 31, 2012, now Pat. No. 8,922,640.

(60) Provisional application No. 61/692,409, filed on Aug. 23, 2012, provisional application No. 61/692,393, filed on Aug. 23, 2012.

(56) References Cited

U.S. PATENT DOCUMENTS

| | | | |
|---|---|---|---|
| 6,317,387 B1 | 11/2001 | D'Amaddio | |
| 6,992,315 B2 * | 1/2006 | Twerdochlib | 250/559.08 |
| 7,068,029 B2 | 6/2006 | Hatcher | |
| 7,271,894 B2 | 9/2007 | Devitt et al. | |
| 7,489,811 B2 * | 2/2009 | Brummel et al. | 382/152 |
| 7,956,326 B1 | 6/2011 | Kychakoff et al. | |
| 8,184,151 B2 * | 5/2012 | Zombo et al. | 348/82 |
| 8,299,785 B2 | 10/2012 | Bousquet et al. | |
| 2004/0051525 A1 | 3/2004 | Hatcher et al. | |
| 2004/0193016 A1 | 9/2004 | Root | |
| 2005/0199832 A1 | 9/2005 | Twerdochlib | |
| 2005/0200355 A1 | 9/2005 | Hatcher | |
| 2006/0088793 A1 | 4/2006 | Brummel et al. | |
| 2007/0129604 A1 * | 6/2007 | Hatcher et al. | 600/136 |
| 2007/0157733 A1 * | 7/2007 | Litzenberg et al. | 73/644 |
| 2007/0296964 A1 | 12/2007 | Nishimura et al. | |
| 2011/0018530 A1 | 1/2011 | Bosquet et al. | |
| 2011/0267428 A1 | 11/2011 | George et al. | |
| 2012/0154594 A1 | 6/2012 | Xie et al. | |
| 2012/0281084 A1 * | 11/2012 | Hatcher et al. | 348/83 |
| 2013/0194412 A1 * | 8/2013 | Hatcher et al. | 348/82 |
| 2013/0194413 A1 * | 8/2013 | Hatcher et al. | 348/82 |
| 2014/0168420 A1 | 6/2014 | Naderhirn | |

OTHER PUBLICATIONS

Co-pending utility U.S. Appl. No. 13/362,417, filed Jan. 31, 2012.

* cited by examiner

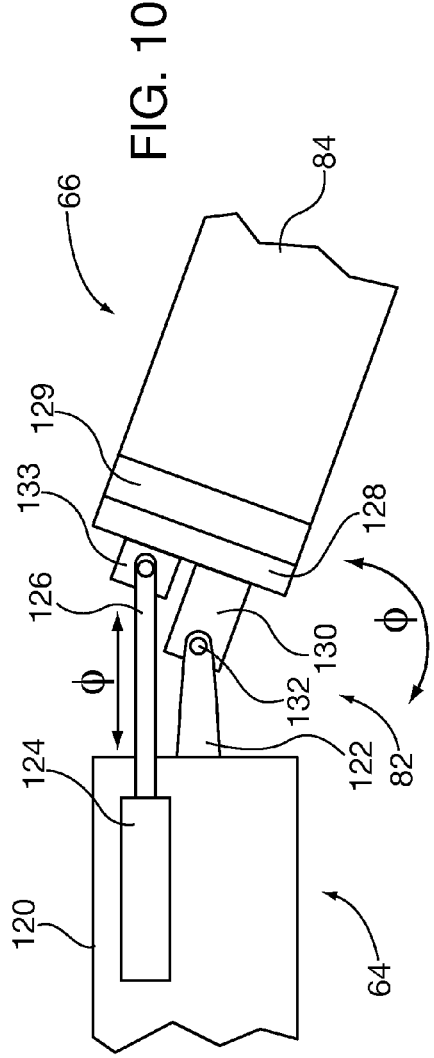
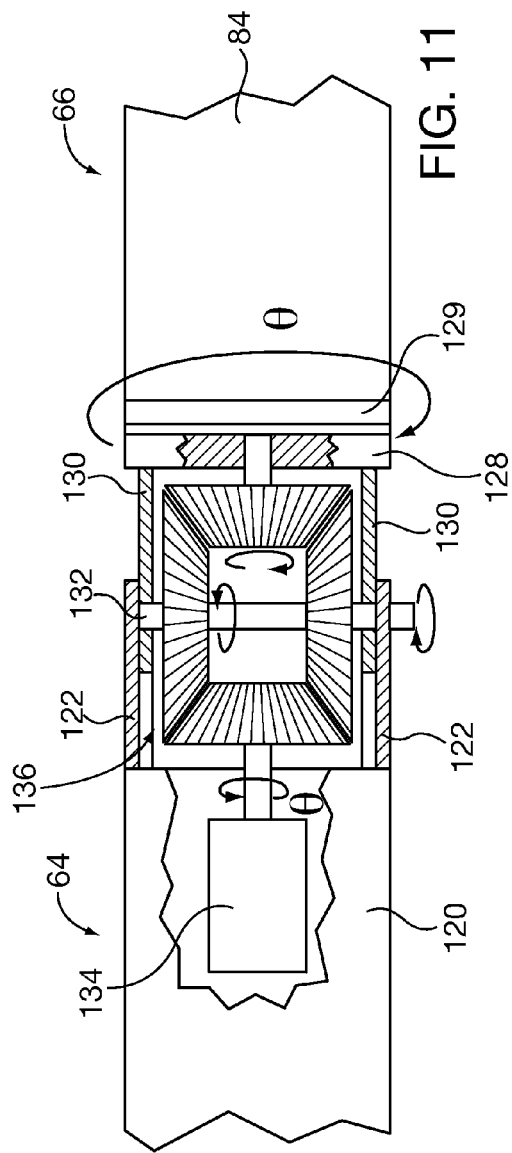

SYSTEM AND METHOD FOR VISUAL INSPECTION AND 3D WHITE LIGHT SCANNING OF OFF-LINE INDUSTRIAL GAS TURBINES AND OTHER POWER GENERATION MACHINERY

REFERENCE TO CO-PENDING APPLICATIONS

This application is a continuation-in-part of U.S. utility patent application entitled "System And Method For Automated Optical Inspection Of Industrial Gas Turbines And Other Power Generation Machinery With Articulated Multi-Axis Inspection Scope", filed Jan. 31, 2012 and assigned Ser. No. 13/362,352.

This application claims the benefit of U.S. provisional patent application entitled "Vision Scope—3D Scanner Tip for Visual Inspection and Measurement" filed Aug. 23, 2012 and assigned Ser. No. 61/692,409, which is incorporated by reference herein.

This application also claims the benefit of the following co-pending U.S. applications: U.S. utility patent application entitled "System And Method For Automated Optical Inspection Of Industrial Gas Turbines And Other Power Generation Machinery", filed Jan. 31, 2012 and assigned Ser. No. 13/362, 417; U.S. utility patent application entitled "System And Method For Automated Optical Inspection Of Industrial Gas Turbines And Other Power Generation Machinery With Multi-Axis Inspection Scope", filed Jan. 31, 2012 and assigned Ser. No. 13/362,387; and co-pending U.S. utility patent application entitled "System And Method For Optical Inspection Of Off-Line Industrial Gas Turbines And Other Power Generation Machinery While In Turning Gear Mode", filed on Aug. 21, 2013, concurrently herewith, Ser. No. 13/971,938, that in turn claims the benefit of U.S. provisional patent application entitled "Hybrid Scope—Turbine Combustor Hardware Visual Inspection Tooling That Can Also Be Used To Inspect The Row 1 Turbine Blades While They Are On Turning Gear (1-1000 rpm)" filed Aug. 23, 2012 and assigned Ser. No. 61/692,393. All of said cited co-pending cited applications are incorporated by reference herein.

BACKGROUND OF THE DISCLOSURE

1. Field of the Invention

The invention relates to optical camera systems for nondestructive internal inspection and real time dimensional measurement of industrial turbines and other power generation machinery, including by way of non-limiting example gas turbines and steam turbines and generators. More particularly aspects of the invention relate to an optical camera inspection system that is capable of manually or automatically positioning the camera field of view (FOV) through a gas turbine combustor nozzle and transition and capturing 3D dimensional data, preferably with additional visual images, of the gas path side of the corresponding combustor support housing, combustor basket and transition with or without human intervention. The invention enables real time dimensional measurement, which is helpful for extracting off-line engineering information about the scanned structures. Three dimensional object shape measurement is performed using projected light patterns generated by a stripe projector and a matrix camera. The scope of the present invention can be configured to perform 3D white light scanning alone or in combination with visual scanning. Automatic camera positioning and image capture can be initiated automatically or after receipt of operator permission.

2. Description of the Prior Art

Power generation machinery, such as steam or gas turbines, are often operated continuously with scheduled inspection and maintenance periods, at which time the turbine is taken off line and shut down. By way of example, a gas turbine engine often will be operated to generate power continuously for approximately 4000 hours, thereupon it is taken off line for routine maintenance, inspection, and repair of any components identified during inspection. Taking a gas turbine off line and eventually shutting it down completely for scheduled maintenance is a multi-day project. Some turbine components, such as the turbine rotor section, are operated at temperatures exceeding 1000° C. (1832° F.). The turbine requires 48-72 hours of cooling time to achieve ambient temperature before complete shutdown in order to reduce likelihood of component warping or other deformation. During the shutdown phase the turbine rotor rotational speed is spooled down from operating speed of approximately 3600 RPM to a speed of approximately 120 RPM or less in "turning gear mode" where the rotor is externally driven by an auxiliary drive motor, in order to reduce likelihood of rotor warping. Other turbine components, such as the turbine housing, are also cooled slowly to ambient temperature.

Once the turbine is cooled to ambient temperature over the course of up to approximately 72 hours internal components of the now static turbine can be inspected with optical camera inspection systems. Known optical camera inspection systems employ rigid or flexible optical bore scopes that are inserted into inspection ports located about the turbine periphery. The bore scope is manually positioned so that its field of view encompasses an area of interest within the turbine, such as one or more vanes or blades, combustor baskets, etc. A camera optically coupled to the bore scope captures images of objects of interest within the field of view for remote visualization and archiving (if desired) by an inspector.

If a series of different images of different areas of interest within a given turbine inspection port are desired, the operator must manually re-position the camera inspection system bore scope to achieve the desired relative alignment of internal area of interest and the field of view. Relative alignment can be achieved by physically moving the bore scope so that its viewing port is positioned proximal a static area of interest. Examples of such relative movement of bore scope and static turbine component are by inserting a bore scope in different orientations within a static combustor or radially in and out of space between a vane and blade row within the turbine section. Relative alignment can also be achieved by maintaining the bore scope viewing port in a static position and moving the turbine internal component of interest into the static viewing field. An example of relative movement of turbine internal component and static bore scope is inspection of different blades within a blade row by manually rotating the turbine rotor sequentially a few degrees and capturing the image of a blade. The rotor is rotated sequentially to align each desired individual blade in the row within the camera viewing field.

Complete turbine inspection requires multiple manual relative repositioning sequences between the camera inspection system viewing port and areas of interest within the turbine by a human inspector. Inspection quality and productivity is subject to the inspection and manipulation skills of the inspector and inspection team. Inspection apparatus positioning is challenging due to the complex manipulation paths between components in a gas turbine. For example, insertion of a bore scope through a combustor inspection port in order to inspect the leading edge of first row vanes or related supports requires compound manipulations. Improper positioning of inspection apparatus within a turbine potentially can damage turbine internal components. Often an inspection team of multiple operators is needed to perform a manual inspection using known inspection methods and apparatus. In summary, known manual camera inspection procedures and inspection system manipulation are time consuming, repetitive in nature, and often require assistance of an inspection team of multiple personnel. The "human factor" required for known manual camera inspection procedures and inspection system manipulation introduces undesirable inspection process variances based on human skill level differences. Given human skill variances, some inspection teams are capable of completing inspections in less time, achieve better image quality and have lower inspection damage risk than other teams. Ideally skills of a high performing inspection team could be captured for use by all teams.

It is also desirable to obtain dimensional information about gas or steam turbines, including gas side internal structures within an industrial gas turbine inspection for extraction of structural information that is useful for off-line engineering studies. For example, it is desirable to obtain structural information about gas side combustor and transition components within the gas side of a gas turbine and generate CAD or other computer images when engineering data files are not available. Previously structural information was obtained by tearing down the turbine after completion of the cool down cycle and thereafter physically inspecting the components with measurement instruments, such as coordinate measurement systems. Physical measurement data were thereafter used to construct CAD or other data files long after engine cool down, thereby adding delay to the maintenance schedule.

It is preferable to gather such structural data prior to turbine tear down so that replacement components can be ordered or fabricated in parallel with the start of maintenance operations rather than wait for visual and/or physical inspection after engine tear down. If dimensional data, preferably with visual data, of turbine internal components can be obtained early and easily in the earliest possible stages of the cool down cycle—for example when the rotor is spinning in the long turning gear mode part of the cool down cycle—components needing repair can be prioritized for replacement, refurbishment and/or other repair days before the turbine rotor comes to a complete rest.

A need exists in the art for optical camera inspection systems and methods that reduce total time necessary to perform a nondestructive internal inspection and gathering of internal dimensional information about power generation machinery, including by way of non-limiting example steam or gas turbines and generators than is attainable by known inspection apparatus and methods that require dismantling and physical measurement of internal components, so that the machinery can be brought back on line for resuming power generation more quickly during maintenance cycles.

Another need exists in the art for optical camera inspection systems and methods that are capable of positioning inspection apparatus within power generation machinery, including by way of non-limiting example steam or gas turbines and generators, consistently and repetitively within an individual machine's inspection cycle or within inspection cycles of multiple different machines, with minimized risk of damage to machine internal components, high image quality, non-physical dimensional measurement and quicker inspection cycling time than is attained by the known manual inspection and component physical dimensional measurement apparatus and methods.

Yet another need exists in the art for optical camera inspection systems and methods that help to equalize inspection skill level and productivity among different inspection teams.

An additional need exists in the art for a camera inspection system that is capable of capturing 3D dimensional data of steam or gas turbine internal components—for example the gas path side of the corresponding combustor support housing, combustor basket and transition in a gas turbine engine, with or without human intervention. Ideally the needed system enables real time dimensional measurement, which is helpful for extracting off-line engineering information about the scanned structures. Preferably the needed system facilitates extraction of dimensional information while the turbine is in cool down mode prior to maintenance and also facilitates gathering of other visual inspection information.

SUMMARY OF THE INVENTION

Accordingly, potential objects of the present invention, jointly or severally among others, are to create optical camera inspection systems and methods for power generation machinery, (including by way of non-limiting example steam or gas turbines and generators) that are capable of capturing 3D dimensional data of steam or gas turbine internal components—for example the gas path side of the corresponding combustor support housing, combustor basket and transition in a gas turbine engine, with or without human intervention. In some embodiments, the needed system enables real time dimensional measurement, which is helpful for extracting off-line engineering information about the scanned structures. In some embodiments the needed system facilitates extraction of dimensional information while the turbine is in cool down mode prior to maintenance and also facilitates gathering of other visual inspection information.

Internal components of power generation machinery, such as gas and steam turbines or generators, are inspected with an optical camera inspection system that is capable of automatically positioning the 3D scanner camera and other system cameras respective fields of view (FOV) to areas of interest within the machinery along a pre-designated navigation path and capturing 3D and/or visual images without human intervention. Automatic camera positioning and image capture can be initiated automatically or after receipt of operator permission. The pre-designated navigation path can be defined by operator manual positioning of an inspection scope within the power machine or a similar one of the same type, and recording the sequence of positioning steps for future replication. The navigation path can also be defined by virtual simulation.

These and other objects are achieved in accordance with the present invention by a system for internal inspection of a gas or steam turbine. In embodiments of the present invention the inspection scope the base is affixed to an off-line gas turbine combustion section, with the inspection scope being inserted through a combustor pilot nozzle port, through the transition, with the 3D scanner camera field of view and any other visual inspection cameras affixed to the scope camera head being oriented to capture images of gas side combustion section internal components, including the combustor and transition.

An embodiment of the present invention features a system for internal three-dimensional scanning inspection of a turbine. The system includes a base for affixation to a turbine inspection port. An inspection scope having an extendable elongated body defines a central axis and has a proximal end that is rotatively coupled to the base. The scope also has a distal end for insertion within a turbine inspection port. The system has camera housing defining a central axis, for insertion within a turbine inspection port. The housing has a proximal end coupled to the inspection scope distal end, and a housing distal end. Coupled to the housing are a structured light 3D scanner having a stripe projector for projecting a band of photons on an inspection surface of interest within a turbine interior, and a matrix camera having an optical path for capturing images of reflected photons that were projected on the inspection surface.

Another embodiment of the present invention features a system for internal three-dimensional scanning inspection of a turbine. The system includes a base for affixation to a turbine inspection port. An inspection scope having an extendable elongated body defines a central axis and has a proximal end that is rotatively coupled to the base. The scope also has a distal end for insertion within a turbine inspection port. A first articulation joint has a first articulation joint proximal end that is rotatively coupled to the inspection scope distal end. The first articulation joint is capable of selective rotation about the inspection scope body central axis. The first articulation joint also has a first articulation joint distal end that is capable of radial displacement relative to the inspection scope body central axis. A camera housing defining a central axis is insertable within a turbine inspection port and has a proximal end coupled to the first articulation joint distal end and defines a camera housing distal end. The camera housing includes a structured light 3D scanner having a stripe projector for projecting a band of photons on an inspection surface of interest within a turbine interior, and a matrix camera having an optical path for capturing images of reflected photons that were projected on the inspection surface. A first camera is coupled to the camera housing, capable of capturing images in a first camera optical path that is generally parallel with the camera housing central axis. A second camera is also coupled to the camera housing, capable of capturing images in a second camera optical path that is generally laterally aligned with the camera housing central axis. The system has a first articulation drive, for articulating the camera housing central axis radially and parallel to the inspection scope central axis that is coupled to the first articulation joint. The system also has a control system, coupled to the first articulation drive, the structured light 3D scanner and the first and second cameras, for positioning the inspection scope and respective camera optical paths along a navigation path within a turbine to an internal area of interest and for selectively capturing respective camera images thereof.

Yet another embodiment of the present invention is directed to a method for performing internal dimensional measurement inspection of a turbine. The method is practiced with a three-dimensional (3D) scanning system that includes a base for affixation to a turbine inspection port and inspection scope that has an extendable elongated body defining a central axis, with a proximal end rotatively coupled to the base and a distal end for insertion within a turbine inspection port. The system used to perform the method has a camera housing defining a central axis, for insertion within a turbine inspection port, having a proximal end coupled to the inspection scope distal end and a structured light 3D scanner. The 3D scanner includes a stripe projector for projecting a band of photons on an inspection surface of interest within a turbine interior, and a matrix camera having an optical path for capturing images of reflected photons that was projected on the inspection surface. The method is practiced with the scanning system by affixing the base to a turbine inspection port. The inspection scope and camera housing are inserted into the inspection port. The turbine is inspected by positioning the inspection scope and camera housing along a navigation path; projecting the band of photons on an inspection surface of interest, and capturing matrix camera images thereof. The inspected turbine's internal dimensional measurements are determined with the matrix camera images.

The objects and features of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which:

FIG. 10 is a schematic elevational view of a camera head articulation and rotation (pan) mechanism of the optical camera inspection system of FIG. 5, showing the Φ and θ degrees of motion;

FIG. 11 is a schematic plan view of a camera head articulation and rotation (pan) mechanism of FIG. 10;

To facilitate understanding, identical reference numerals have been used, where possible, to designate identical elements that are common to the figures.

DETAILED DESCRIPTION

After considering the following description, those skilled in the art will clearly realize that the teachings of the present invention can be readily utilized for inspection of internal components of gas or steam turbines with a 3D scanning camera inspection system that is inserted and positioned within the turbine, for example through a gas turbine combustor nozzle port. Three dimensional internal component measurements are performed using projected light patterns generated by a stripe projector and a 3D white light matrix camera. Real time dimensional information is gathered without physical contact, which is helpful for extracting off-line engineering information about the scanned structures. Exemplary 3D scans, preferably with additional visual images, are performed of the gas path side of a gas turbine combustor support housing, combustor basket and transition with or without human intervention. Preferably, internal components of gas and steam turbines can also be visually inspected an optical camera inspection system that is optionally incorporated with the 3D scanner. The system of the present invention optionally is capable of automatically or manually positioning the 3D and/or visual cameras respective fields of view (FOV) to an area of interest within the turbine along a pre-designated navigation path and capturing images with or without human intervention. Said camera positioning and image capture can be initiated automatically or after receipt of operator permission. The inspection system includes an articulated multi-axis inspection scope with an optical camera that may be inserted through a gas turbine engine combustor nozzle access port, combustor and transition, or internal components of many types of turbines.

In some embodiments, the optical camera inspection system is capable of automatically positioning the respective 3D and optical cameras fields of view (FOV) to an area of interest within the machinery and capturing images without human intervention. Automatic camera positioning and image capture can be initiated automatically or after receipt of operator permission. Alternatively, the system may be human-operated in "manual" mode.

Camera Inspection System Overview

Figure 1:
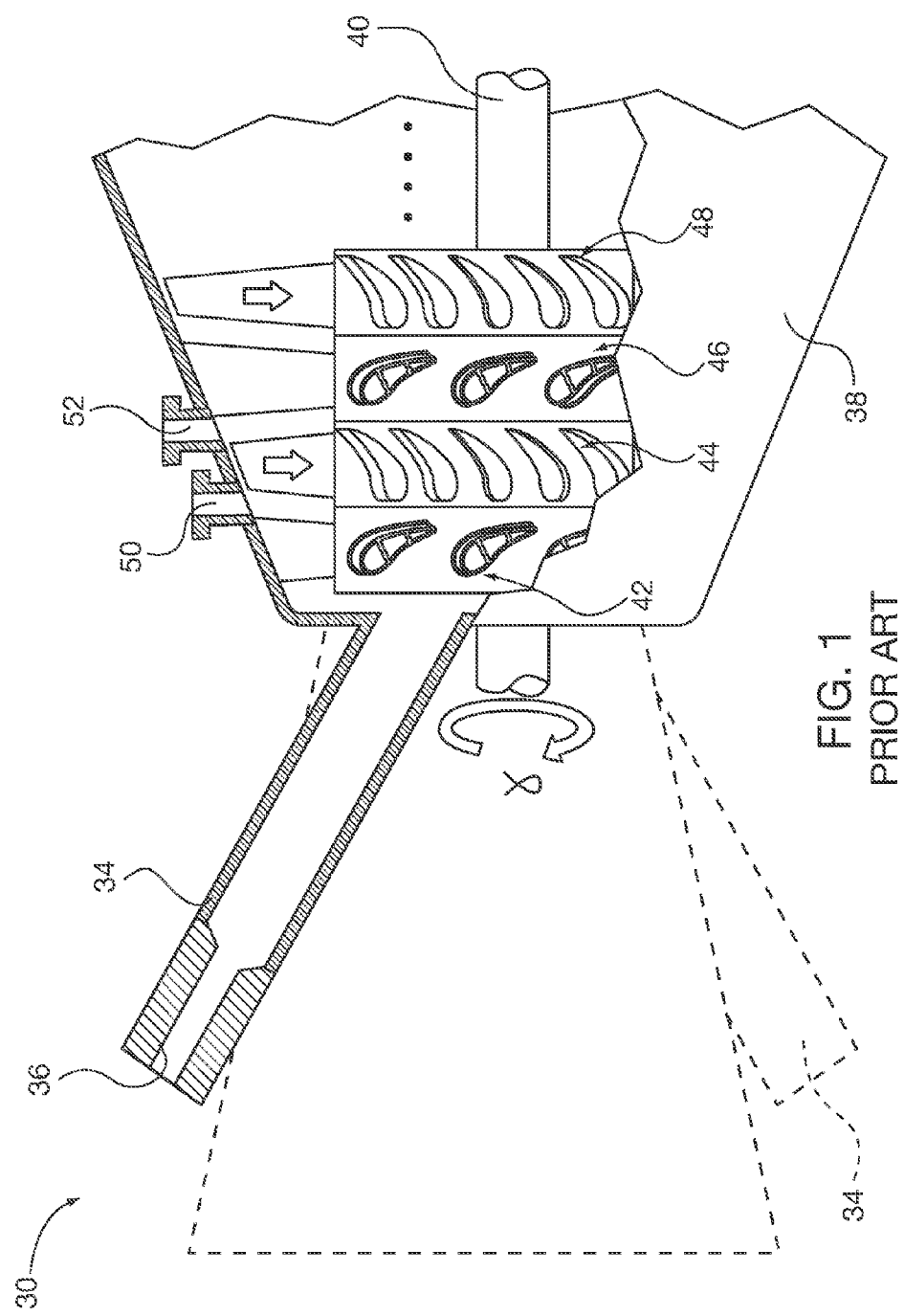
FIG. 1 is a partial cross sectional schematic view of a known gas turbine, including its combustion section.

Referring to FIG. 1, embodiments of the present invention facilitate automated off-line remote 3D dimensional scanning and optional visual inspection of gas turbine 30 internal components, including combustion section combustors and transitions 34. As shown in FIGS. 2-4 and 21-26, embodiments of the present invention inspection system enables inspection of offline turbines that have not fully cooled to ambient temperature by attaching remote-actuated 3D scanner and optional camera inspection scope probes 60, to turbine inspection ports such as a combustor nozzle port 36 and acquiring visual and/or 3D scanning data, for example of a transition component internal surface 37. Upon attachment the inspection scope probes 60 are selectively positioned (manually by an operator or automatically without an operator) via internal motion control servo motors that are under command of a motion control system. Three dimensional scan and optional visual image data are acquired, captured, and if desired archived for further analysis.

Articulated Inspection Scope

Figure 2:
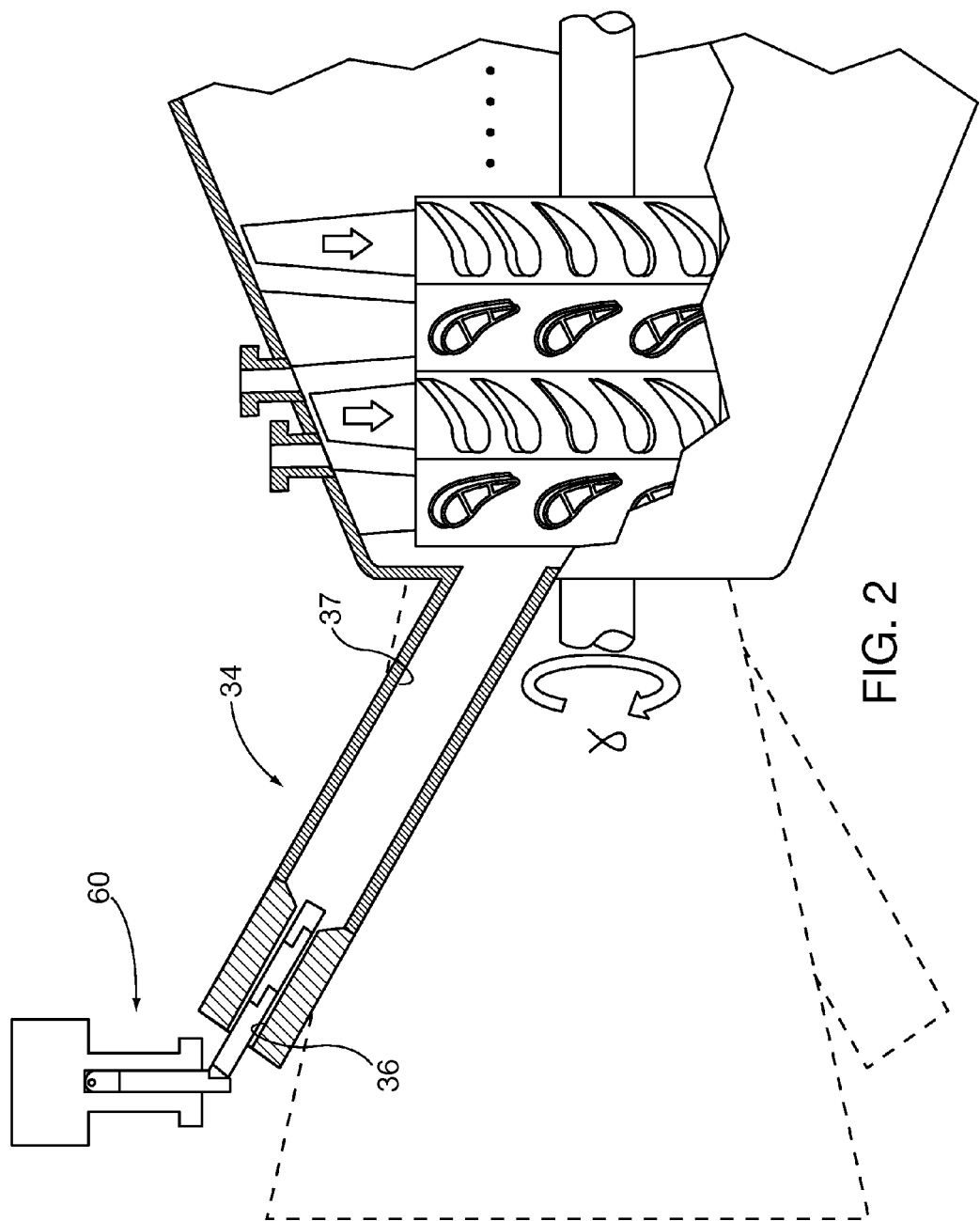
FIG. 2 is a partial cross sectional schematic view of a known gas turbine showing partial insertion of an optical camera inspection system described in the present application into a combustor nozzle port.
Figure 3:
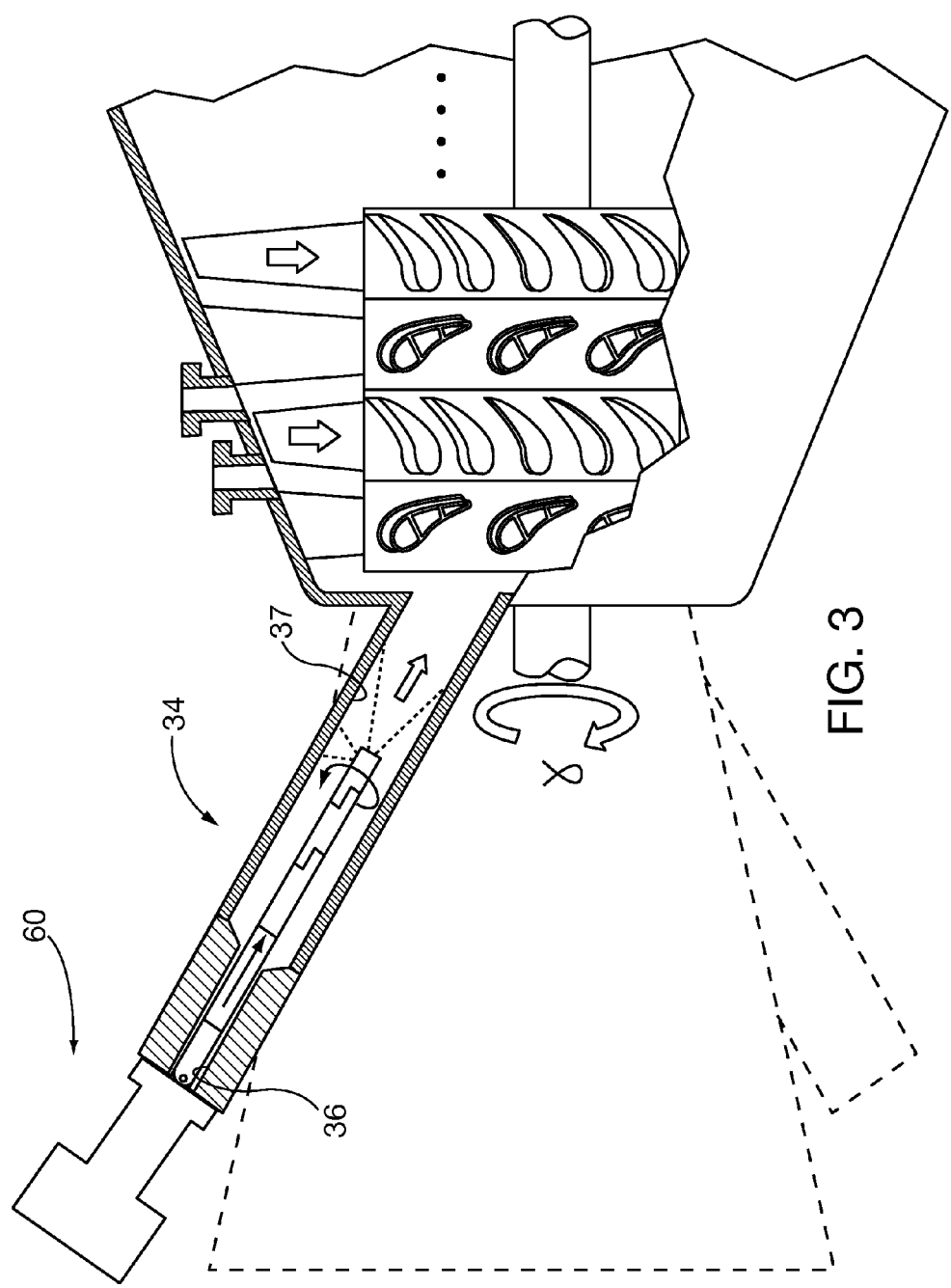
FIG. 3 is partial cross sectional schematic view of a known gas turbine performing an inspection of a combustor internal components with the inspection system of FIG. 2.
Figure 4:
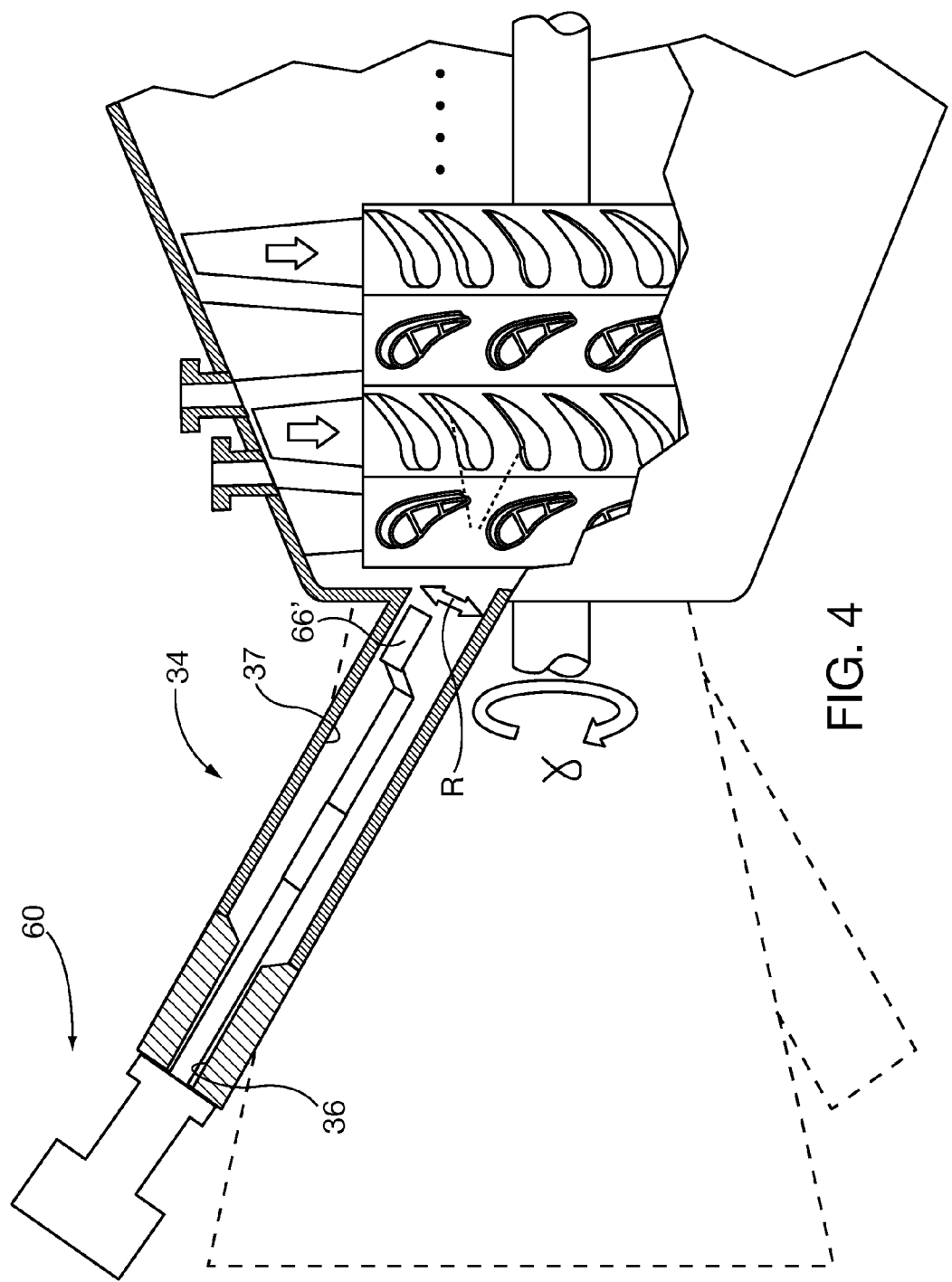
FIG. 4 is partial cross sectional schematic view of a known gas turbine performing a 3D scanning inspection of a transition component dimensions with the 3D scanning inspection system of the present invention.

FIGS. 2-4 show inspection of an off-line gas turbine by insertion (FIG. 2) of an articulated inspection scope embodiment 60 into a combustor nozzle port 36 that functions as an inspection port. For maneuvering clearance of the scope 60 about the confines of a gas turbine installation, inspection scope 60 has a folding knuckle, so that the scope can be folded into a generally L-shape profile about half as long as an elongated scope. Once the 60 is positioned within the inspection port 36, the knuckle is straightened, as shown in FIG. 3. After the inspection scope 60 is affixed to the inspection port 36 it may be utilized to inspect to combustor and transition internal components by rotating and extending its camera head. In FIG. 4, as the 3D scanning system embodiment scope 60, subsequently described in greater detail herein with reference to FIGS. 21-26, is further extended and its camera head articulated dimensional data and optional images of the combustion section transition inner surface 37 may be acquired.

Figure 5:
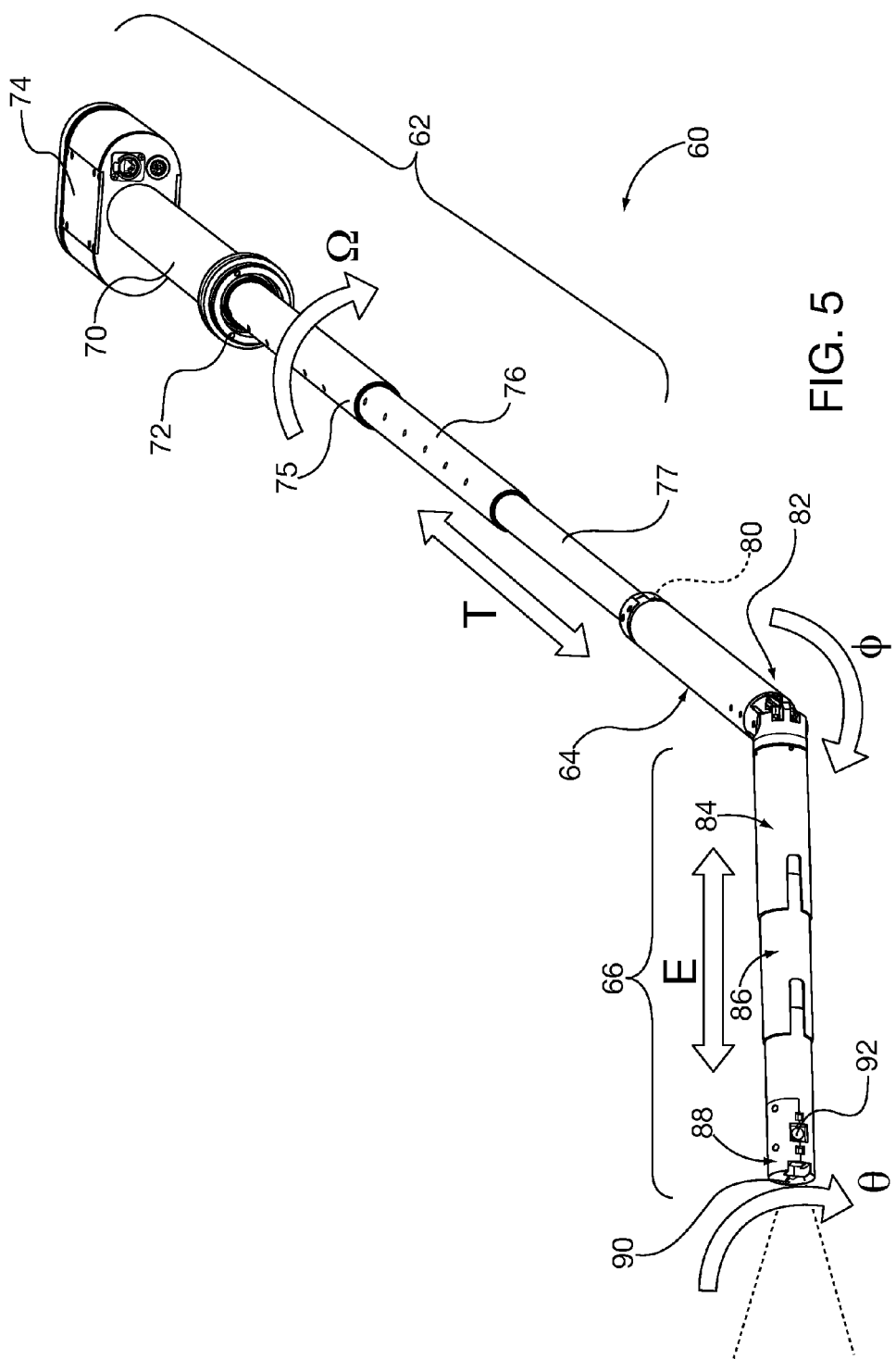
FIG. 5 is a perspective schematic view of the optical camera inspection system of the embodiment of FIG. 2, showing available degrees of motion Ω, T, Φ, E and θ.

Referring to FIG. 5, the inspection scope 60 has three main component sections: extension tube section 62 (see FIGS. 5-9); motor can 64 (FIGS. 5, 10-12); and camera tip 66 or head (FIGS. 5, 12-15 and 22-25) that are capable of performing the following five degrees of motion freedom:

Ω—gross rotation;
T—telescoping extension;
Φ—camera head articulation;
E—camera head tip extension; and
θ—camera head rotate/pan.

The extension tube section 52 has a mounting tube 70 and mounting collar 72 that are attached to an inspection port, such as the combustor nozzle port 36. Motor housing 74 is attached to the opposite end of mounting tube 70 distal the mounting collar 72 and houses the servo motors necessary to perform the Ω and T degrees of motion. Three telescoping tubes 75-77 collapse into the mounting tube 70 for providing the T directional motion.

Figure 6:
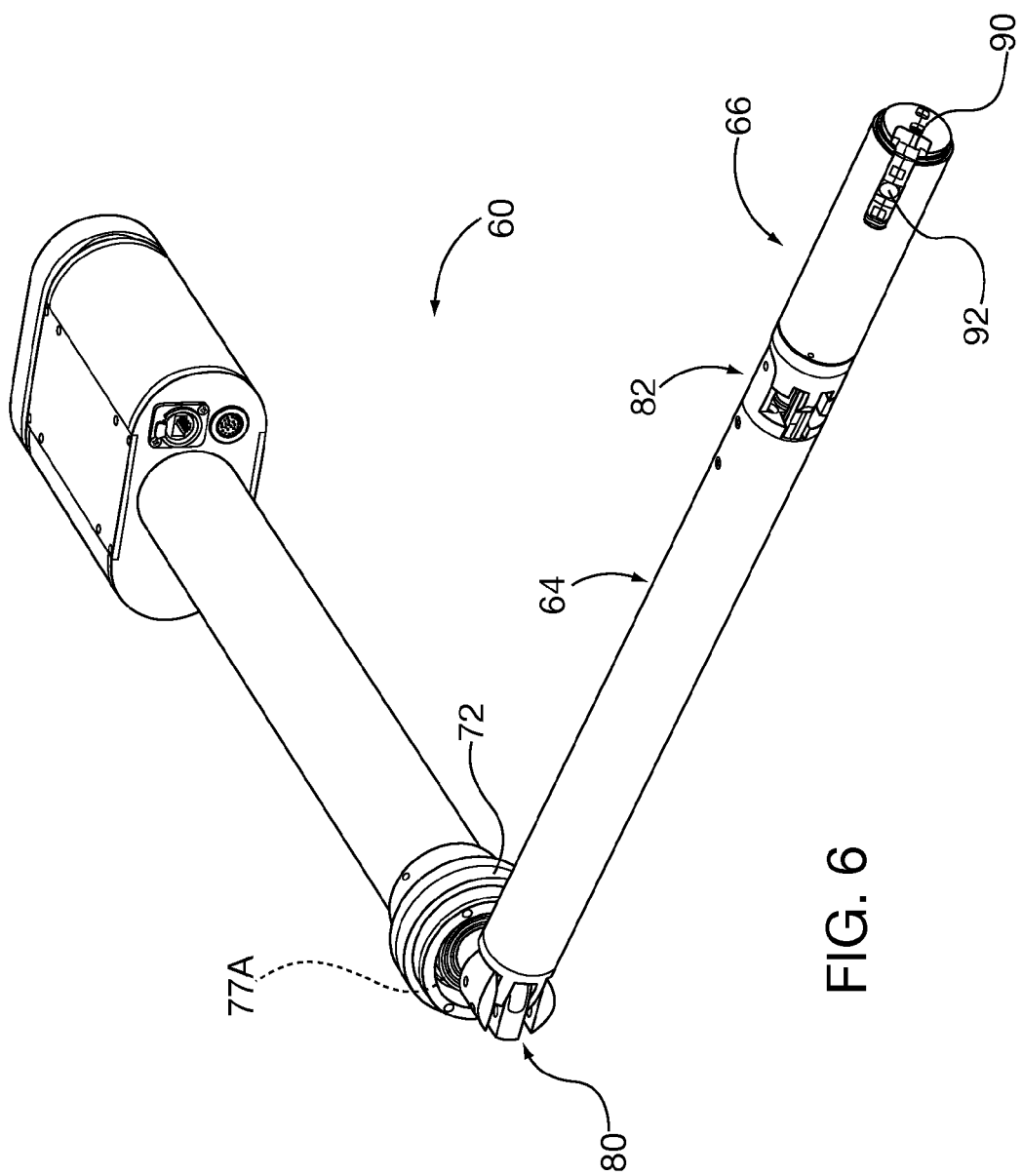
FIG. 6 is a perspective schematic view of the optical camera inspection system of FIG. 5, in the folded insertion position of FIG. 2.
Figure 7:
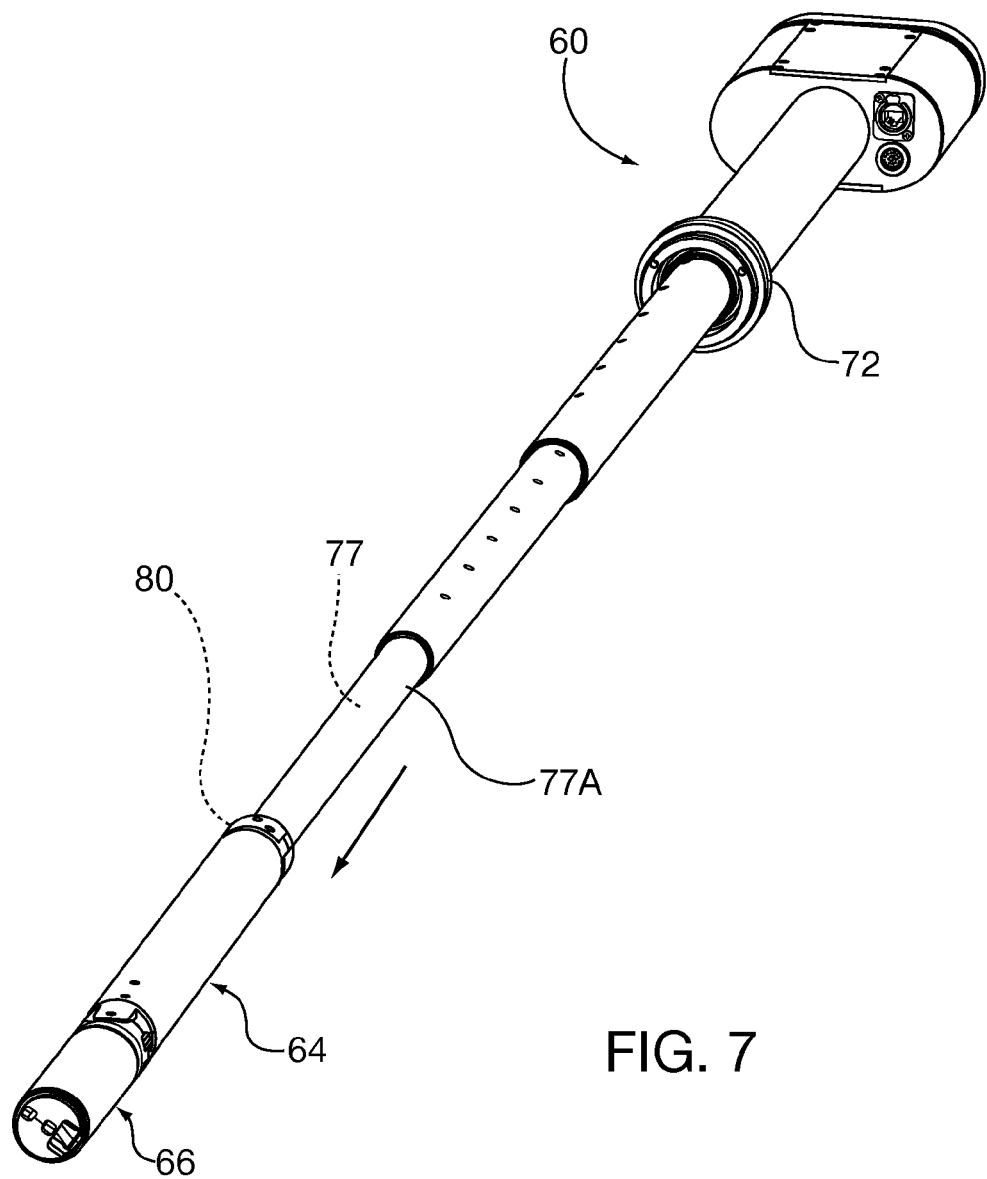
FIG. 7 is a perspective schematic view of the optical camera inspection system of FIG. 5, in the locked inspection position of FIG. 3.

As shown in FIGS. 6 and 7, spring loaded locking knuckle 80 enables the entire inspection scope 60 to fold for compact maneuvering about the turbine 30, as shown in FIG. 2 and described above. Locking sleeve 77A slides over telescoping tube 77 and restrains knuckle 80 therein when the inspection scope 60 is in is locked inspection position as shown in FIG. 7.

As shown in FIG. 5, motor can 64 houses the servo motors necessary to position motorized articulating joint 82 that provides the Φ degree of motion, the camera head 66 head extension motion E via the camera head telescoping extensions 84, 86 and the camera head 88 rotate/pan degree of motion θ. The camera head 88 includes camera ports 90, 92 for respective axial and lateral fields of view (FOV).

Figure 8:
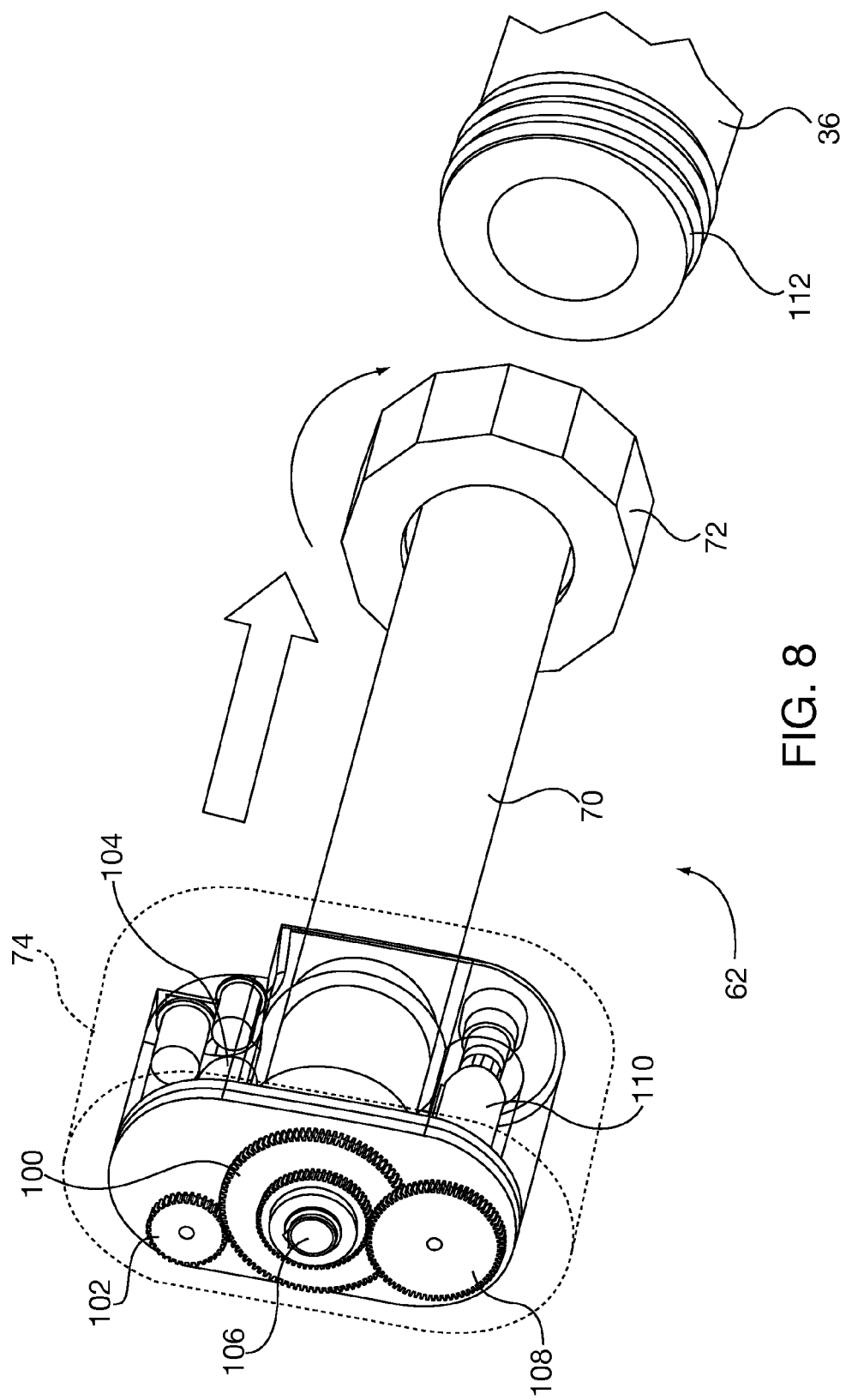
FIG. 8 is a perspective schematic view of the extension tube mechanism portion of the optical camera inspection system of FIG. 5, showing the Ω and T degrees of motion.
Figure 9:
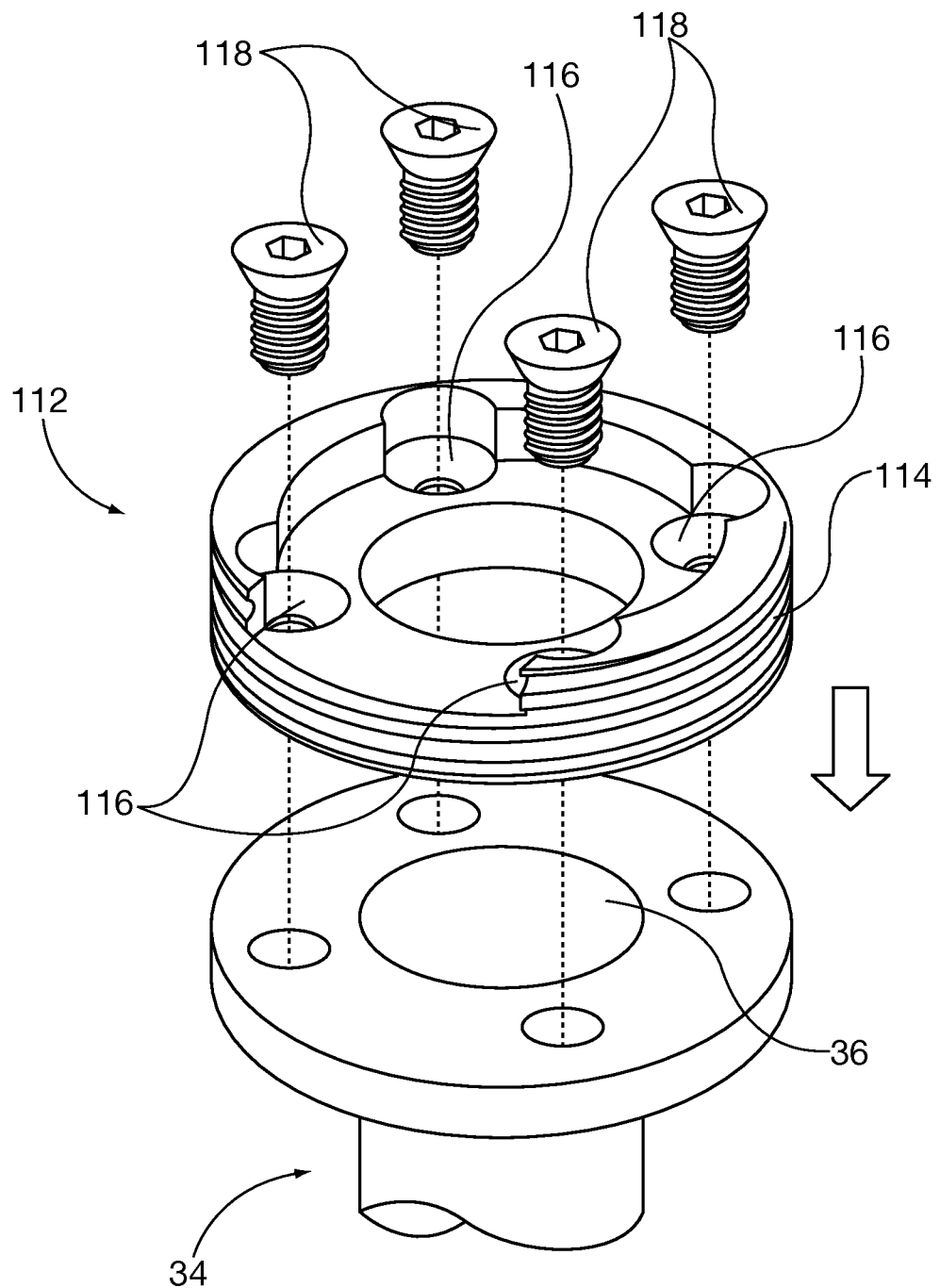
FIG. 9 is a schematic perspective view of an adapter ring of the present invention being attached to a turbine inspection port.
Figure 12:
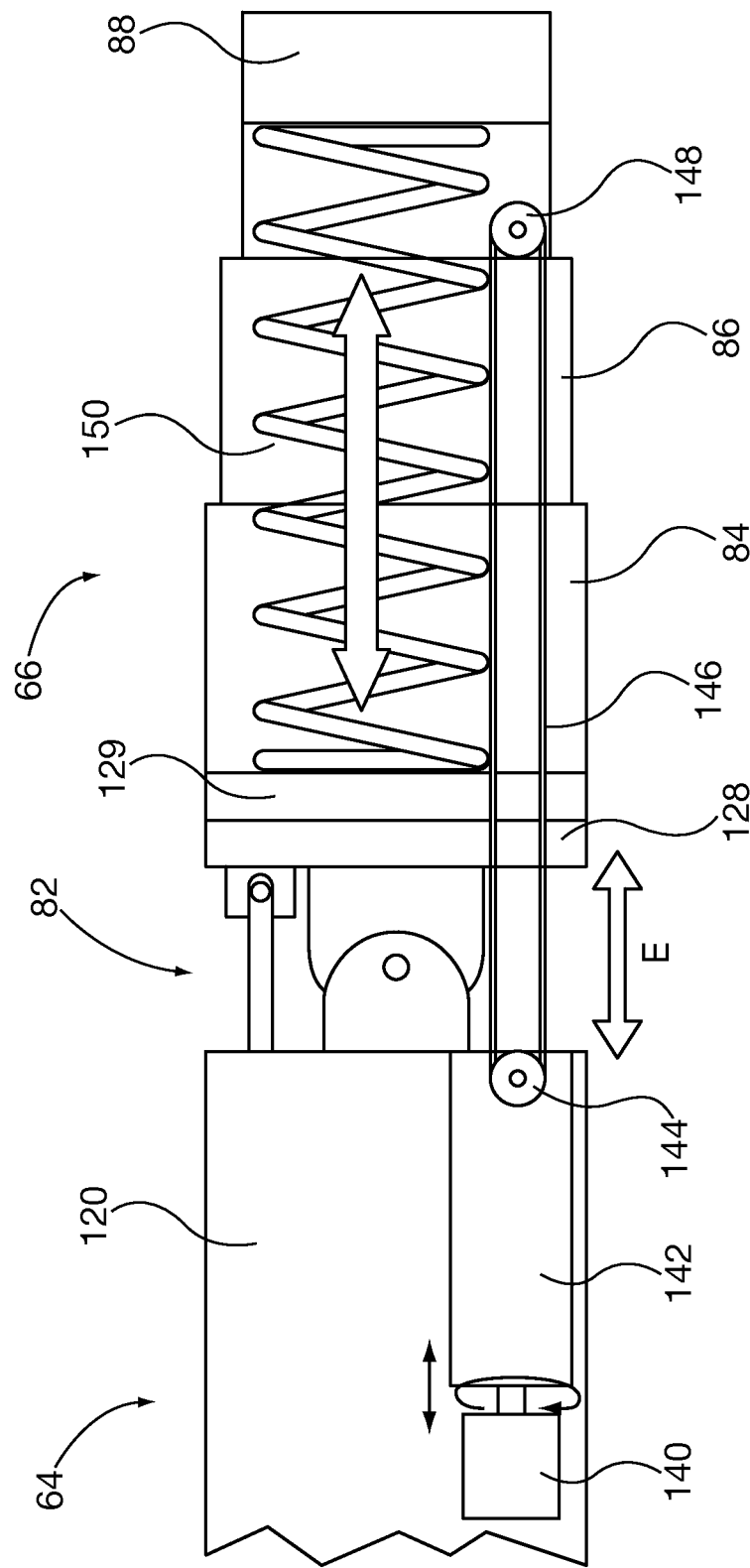
FIG. 12 is a schematic elevational view of a camera head extension mechanism of the optical camera inspection system of FIG. 5, showing the E degree of motion.

FIG. 8 is a detailed view of the motor housing 74, showing two coaxially nested, independently driven large and small diameter gears in the rotation hub 100. Rotate drive gear 102 is driven by the rotate servo motor 104, for effectuating the Ω motion by rotating the larger diameter gear in the rotation hub 100. Telescope extension drive screw 106 is rigidly coupled to the smaller diameter gear in rotation hub 100, that in turn engages the extend drive gear 108. Extend servo motor 110 is responsible for effectuating the T motion by rotating the smaller diameter in the rotating hub 100. Mounting collar 72 attaches to adapter ring 112, that is in turn attached to an inspection port, such as the combustor nozzle inspection port 36. As shown in FIG. 9, the adapter ring includes a plurality of peripheral threads 114 that are engaged with mating internal threads within the collar 72. The adapter ring 112 has mounting holes 116 for receipt of tapered head machine screws 118. The screws 118 may be captively mounted within adapter ring 112. Other configurations of adapter ring or other forms of base that affixes the scope to an inspection port may be substituted for the adapter ring 112.

Referring to FIG. 10, motor can 64 has a motor can housing 120 with a pair of spaced apart ear-like motor can pivots 122. Articulate motion servo motor 124 rotates drive screw 126 that imparts the Φ articulating motion by tipping camera pivoting hub 128. The tipping motion axis 132 is established between camera hub pivot 130 that is rotatively coupled to the motor can pivot 122. Offset link 133 is coupled to drive screw 126 and converts linear motion to rotational motion about tipping motion axis 132.

Motor can housing 120 also contains camera pan/rotate servo motor 134 that imparts the θ degree of motion on camera head 66, as shown in FIG. 11. Servo motor 134 drives bevel gear train 136, which in turn includes the driven bevel gear that is rotatively captured within camera pivoting hub 128, for in turn rotating the rotating hub 129. The rotating hub 129 is rigidly coupled to the camera head telescoping extension 84. Camera tip telescoping extensions 84 and 86 are extended and retracted in the E motion degree by extension servo motor 140 that in turn engages linear drive screw 142. The drive screw 142 includes drive pulley 144, over which passes tensioned cable 146. Slave pulley 148 is attached to camera head 88 and is also coupled to cable 146. Coil spring 150 is interposed between camera head 88 and rotating hub 129, and biases them away from each other, thereby tensioning cable 146. It follows that selective translation of the drive screw 142 by the extension servo motor 140 moves the camera head 88 to the left and right in the figure (motion E).

Figure 13:
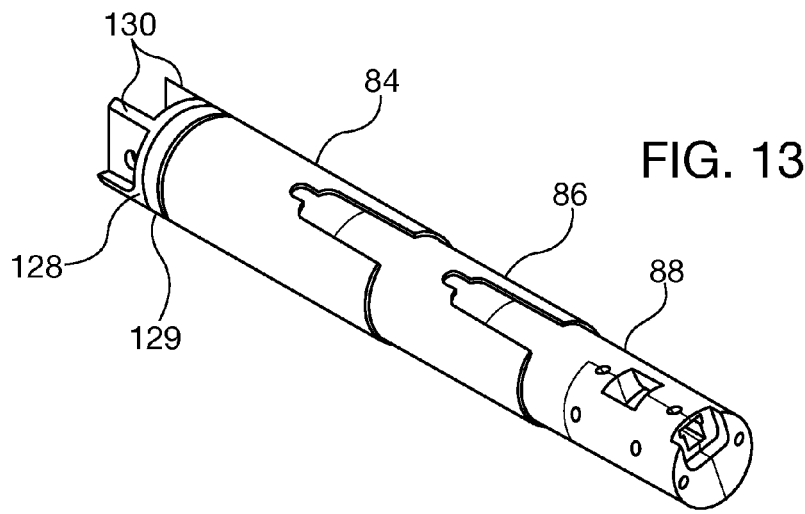
FIG. 13 is a schematic perspective view of the camera head of the optical camera inspection system of FIG. 5.
Figure 14:
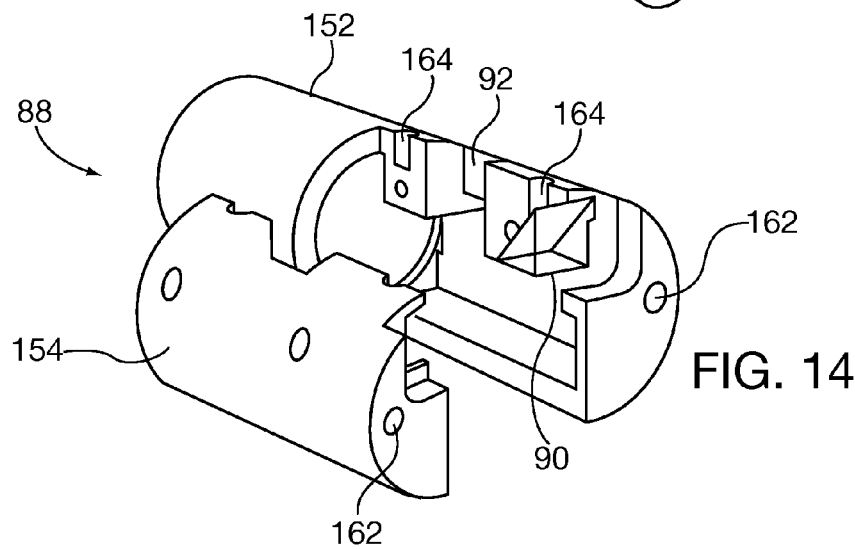
FIG. 14 is a schematic exploded perspective view of a camera head of the optical camera inspection system of FIG. 5.
Figure 15:
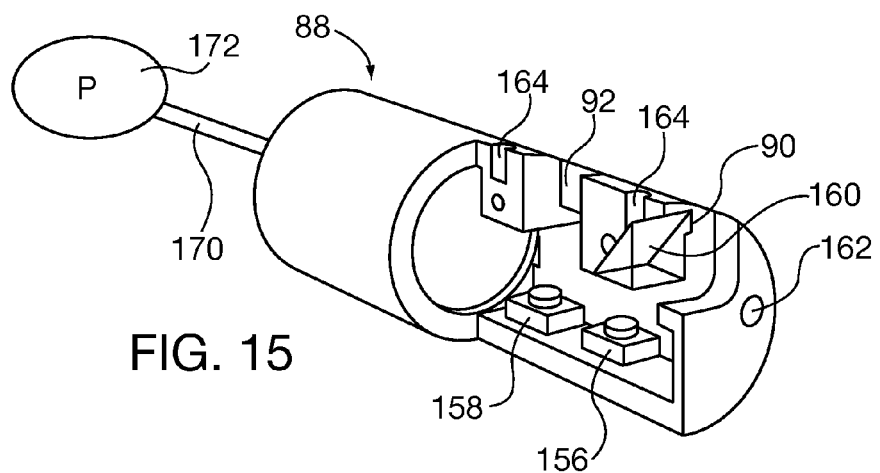
FIG. 15 is a schematic partial assembly perspective view of the camera head of FIG. 14.

FIGS. 13-15 show the camera head 88 that has a clamshell construction with camera head housing 152 and selectively removable cover 154. Camera 156 has a field of view (FOV) through "camera 1" port 90, extending along the central axis of the camera head 88. Camera 158 has a field of view (FOV) through "camera 2" port 92, extending laterally or normal to the central axis of the camera head 88. Camera 156 generates its image through prism 160. Cameras 156, 158 are known auto-focusing USB cameras of the type routinely used with personal computers. Light emitting diodes (LEDs) 162 and 164 provide illumination for the cameras 156, 158 during internal inspection of power generation machinery. One or two cameras having different resolution and focus properties may be substituted for auto-focusing USB cameras. Similarly the camera head illumination system may employ LEDs or other illumination sources of desired output intensity or other characteristics, including by way of non-limiting example steady-state or strobe illumination, variable or dimmable intensity outputs.

Three-Dimensional Scanning Camera Inspection Scope

Figure 21:
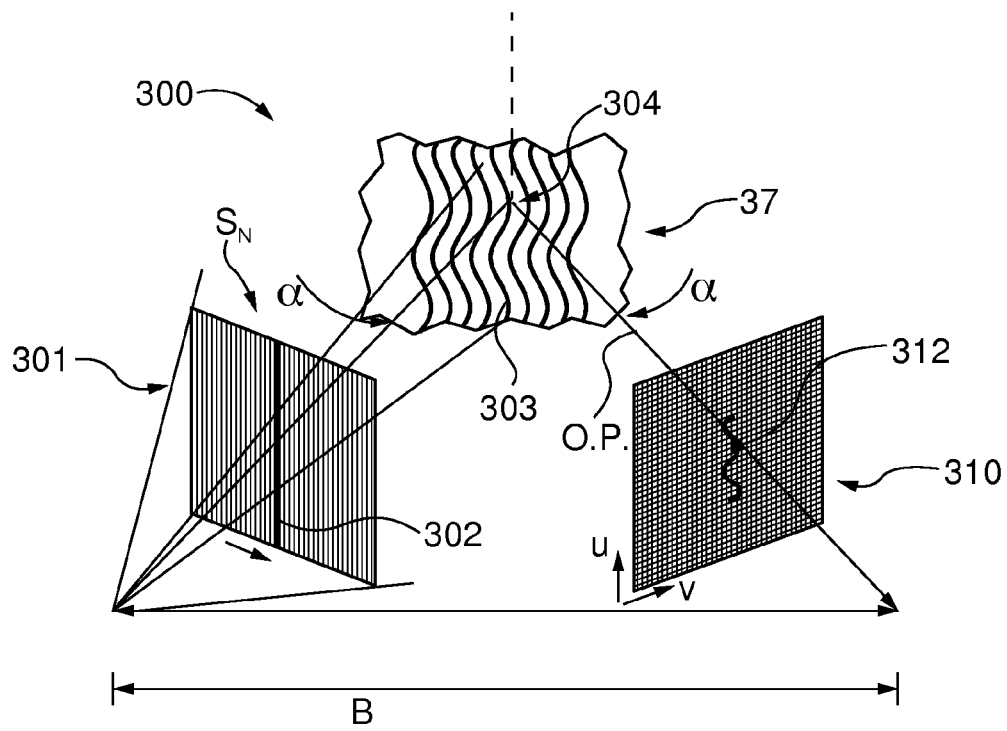
FIG. 21 is a perspective schematic view showing the operational principles of non-contact 3D dimensional scanning performed by the inspection system of the present invention.
Figure 24:
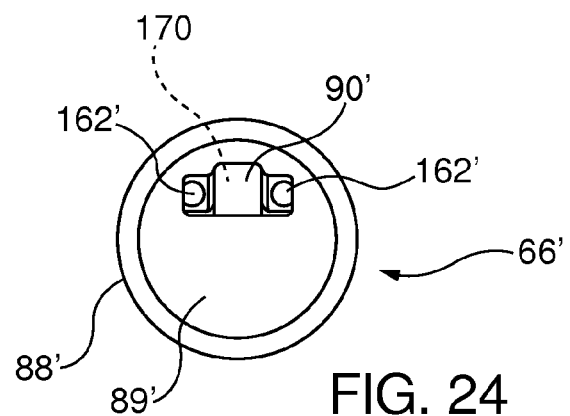
FIG. 24 is a schematic elevational view of the camera head distal tip of the inspection system of FIG. 22.

In the present invention, the 3D scanning camera inspection scope 60 measures the three-dimensional shape of an internal component within a turbine, such as a gas turbine transition 37, without physical contact. Referring to FIG. 21, component shape measurement is performed with a 3D scanner 300, by applying known principles of projected light patterns generated by a stripe projector 301 having a two dimensional array $S_N$ of projected stripes 302 and a scanning camera 310 that has a u×v pixel matrix. Projecting a narrow band of light $S_N$ with the projector 301 onto a three-dimensionally shaped surface, such as transition 37, produces a line of illumination 303 that appears distorted from other perspectives than that of the projector 301. For example, line of illumination 303 illuminates object pixel 304 on the shaped surface of transition 37 and its reflection is captured by the matrix camera 310 as camera pixel 312. The series of corresponding camera pixels that capture the reflection is used for an exact geometric reconstruction of the surface shape and can be performed using known commercially available hardware and reconstruction software. For example, in FIG. 21 the three dimensional shape of the line of object pixels 304 along illumination line 303 is determined by the positions of the corresponding captured image of camera pixels 312, the triangulation base distance B and the angle α of incidence and reflection along the optical path (O.P.).

The present invention 3D scanning camera inspection scope substitutes alternative embodiment motor can 64', camera tip or head 66' and articulated joint 82' (with related drive) shown in FIGS. 22-25 for the motor can 64, tip or head 66 and articulation joint 82 (with related drive) that are described in prior FIGS. 10-15. Camera head 66' is coupled to a camera hub 128', which forms the distal end of articulation joint 82'. Camera hub 128' is pivotally coupled to respective distal ends of a pair of parallel links 131' at joint 130'. The proximal ends of links 131' are pivotally coupled to the motor can pivots 122' for mechanical coupling of the motor can 64' and camera tip or head 66'.

Figure 23:
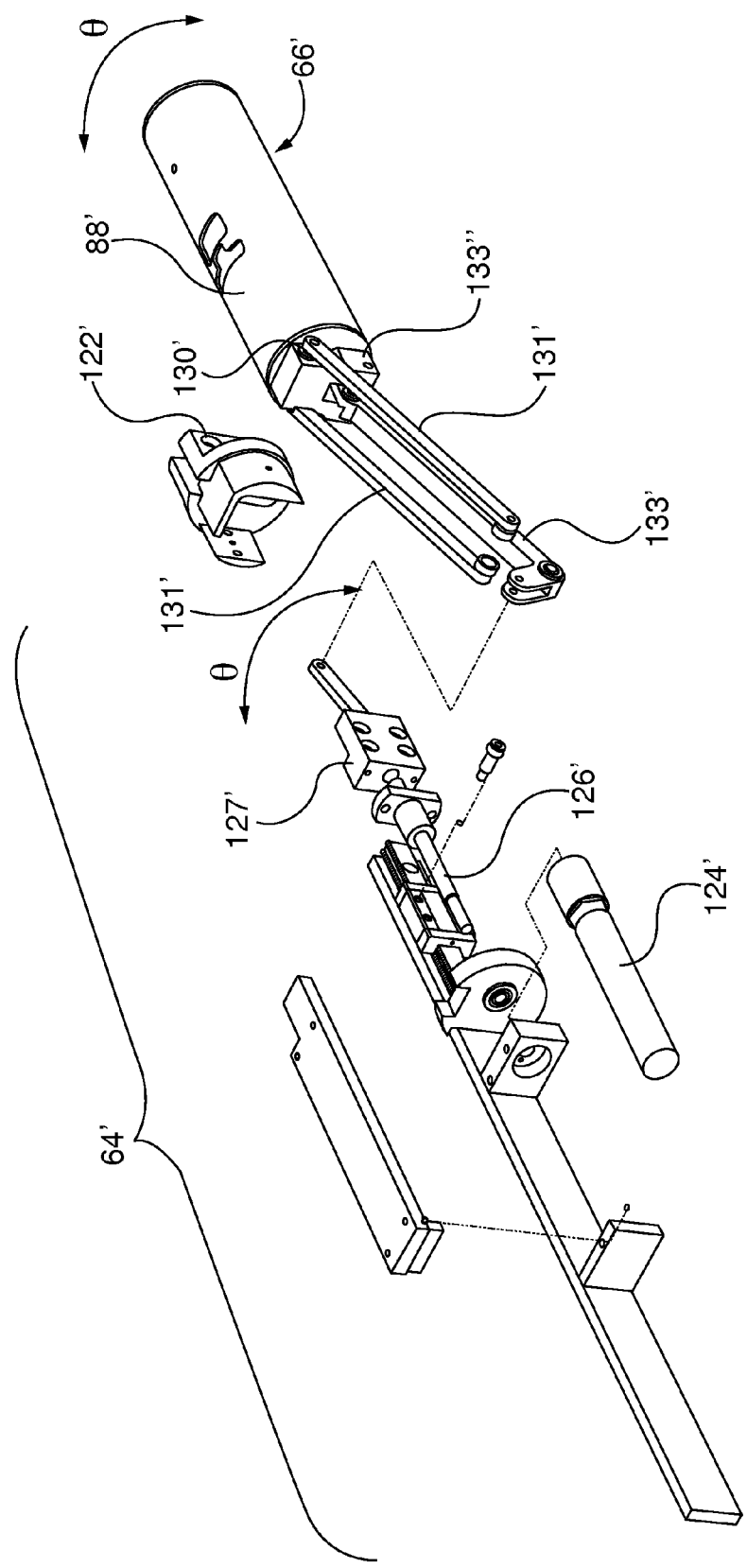
FIG. 23 is an exploded schematic view of the camera head articulation joint mechanism of the inspection system of FIG. 22.

In order to drive the arcuate range of motion φ, a modified version of the previously described inspection scope system tube section 62 and motor can 64' components upstream of the articulation joint 82' are utilized with the alternative embodiment camera head 66', which are shown in exploded view in FIG. 23. Motor 124' rotates drive screw 126'. Crank assembly 127' converts drive screw 126' rotary motion to arcuate motion φ. A distal tip of crank assembly 127' is rotatively coupled to a proximal end of offset link 133'. The distal end of offset link 133' is pivotally coupled to the camera hub 128'. It is preferable that the kinematic geometry of the parallel links 131', offset link 133' and their respective relative pivotal connection positions 122', 130' and 133" with respect to the central axes of the motor can 64' and camera head 66' are chosen so that both central axes remain parallel to each other throughout the range of motion φ. However, other kinematic geometries may be utilized.

FIGS. 22-25 show the camera head 66' that includes camera hub 128', an outer housing 88'and distal tip 89'. Forward visual inspection camera 156' has a field of view (FOV 156') through "camera 1" port 90', extending along the central axis of the camera head 66'. Side viewing visual inspection camera 158' has a field of view (FOV 158') through "camera 2" port 92', extending laterally or normal to the central axis of the camera head 66'. Camera 156' generates its image through prism 160'. Similarly, camera 158' generates its image along optical path (O.P.) through beam splitter 161' that it shares with scanning camera 310. As will be described in greater detail below cameras 158' and 310' are utilized in separate respective visual and 3D scanning modes of operation, so sharing a common optical path advantageously reduces internal volume of the camera head 66'. Cameras 156', 158' are known auto-focusing USB cameras of the type routinely used with personal computers. Cameras having different resolution and focus properties may be substituted for auto-focusing USB cameras.

Figure 22:
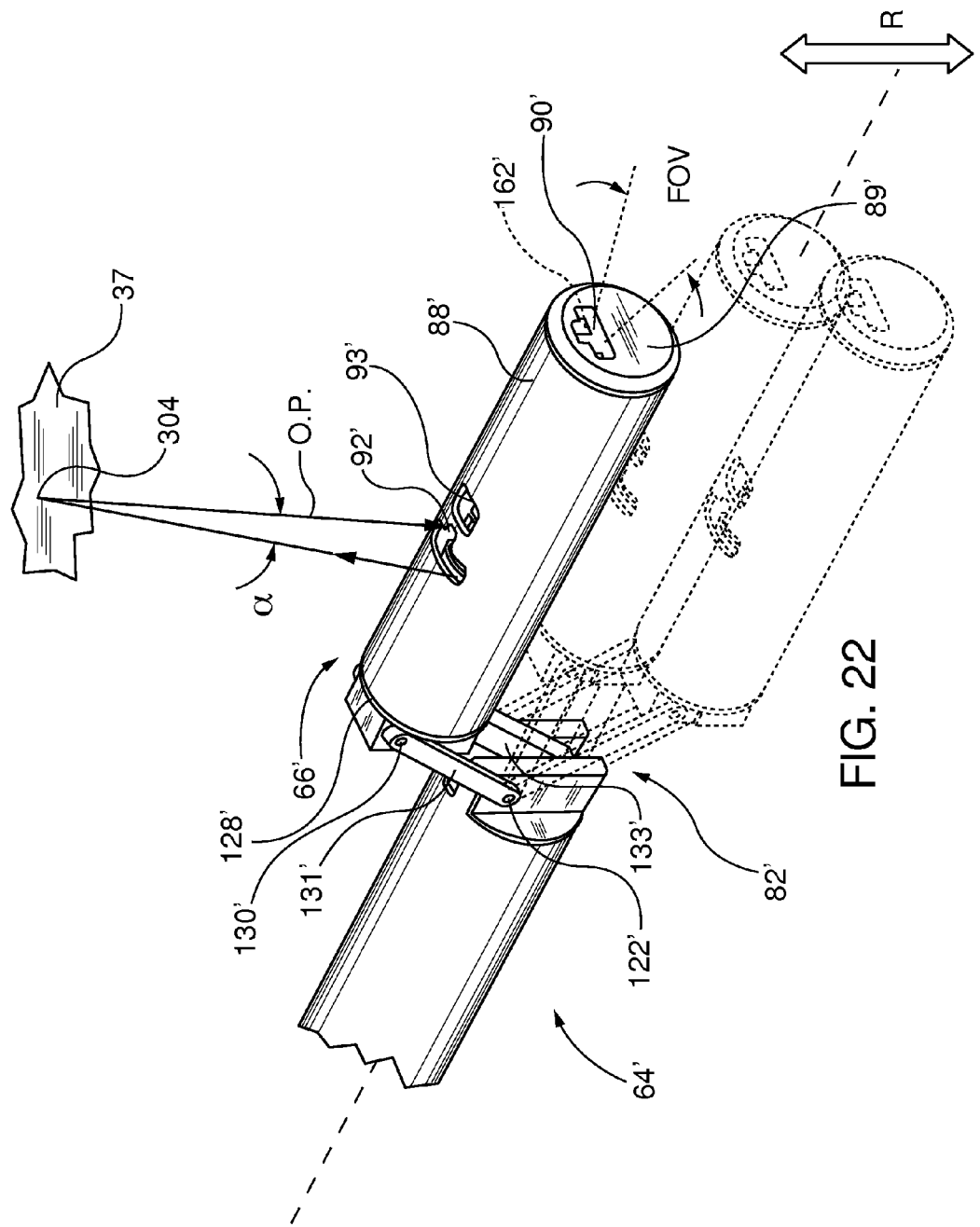
FIG. 22 is a perspective view of the range of motion of a camera head of the non-contact 3D dimensional scanning inspection system of the present invention.

The 3D scanning system 300 components within the camera head 66' comprise the projector 301 and 3D camera 310. Exemplary projectors and 3D cameras are available from XIMEA Corp. of Golden, Colo., USA. The projector 301 projects a light beam along an optical path through prism 305 that exits the camera head outer housing 88' through aperture 92'. In an exemplary embodiment of the present invention, the projector 301 and the 3D camera 310 are oriented so that incident projected light converges with the camera 310 O.P. at an angle α of 10 degrees and an optical path length of 3.94 inches (100 mm). Incident and convergent light pass through optical port 92' that is formed within the housing 88'. In order to aid alignment of the camera head at the desired distance of 100 mm from an inspection surface, such as transition 37, a diode laser 320, that is in visual communication with the laser port 93' formed within the camera housing 88', projects a focus dot 321 on the transition 37 surface. The desired O.P. distance of 100 mm is achieved when the laser dot is in focus of camera 310. The camera head 66' is aligned relative to the transition surface 37 by articulating the articulation joint mechanism 82' articulation angle Φ. This in turn translates the camera head 66' radially relative to the scope 60 central axis along the direction R, as shown in FIGS. 4 and 22. The inspection system may automatically orient the camera head 66' along the radial direction R through a known feedback loop until the laser spot 321 is focused. Upon achieving desired laser spot 321 focus, spot projection by laser 320 is ceased prior to commencement of a 3D scanning procedure.

An illumination system, shown comprising pairs of light emitting diodes (LEDs_lights 162' and 164'are respectively mounted co-axial and transverse with the camera head 66' central axis. They provide illumination for the cameras 156', 158' during internal visual inspection of power generation machinery. The LED lights 162' and 164' may be oriented in any desired position relative to the camera head 66' central axis The camera head illumination system may employ LEDs or other illumination sources of desired output intensity or other characteristics, including by way of non-limiting example steady-state or strobe illumination, variable or dimmable intensity outputs. The illumination system is not utilized when performing dimensional scans with the 3D scanning system 300 or when projecting a focusing spot 321 with the laser 320. Thus, if desired, the illumination system LED lights 162', 164' and laser 320 may share a common power source and lighting control system (see, e.g., FIG. 26).

Inspection Scope Cooling System

Figure 25:
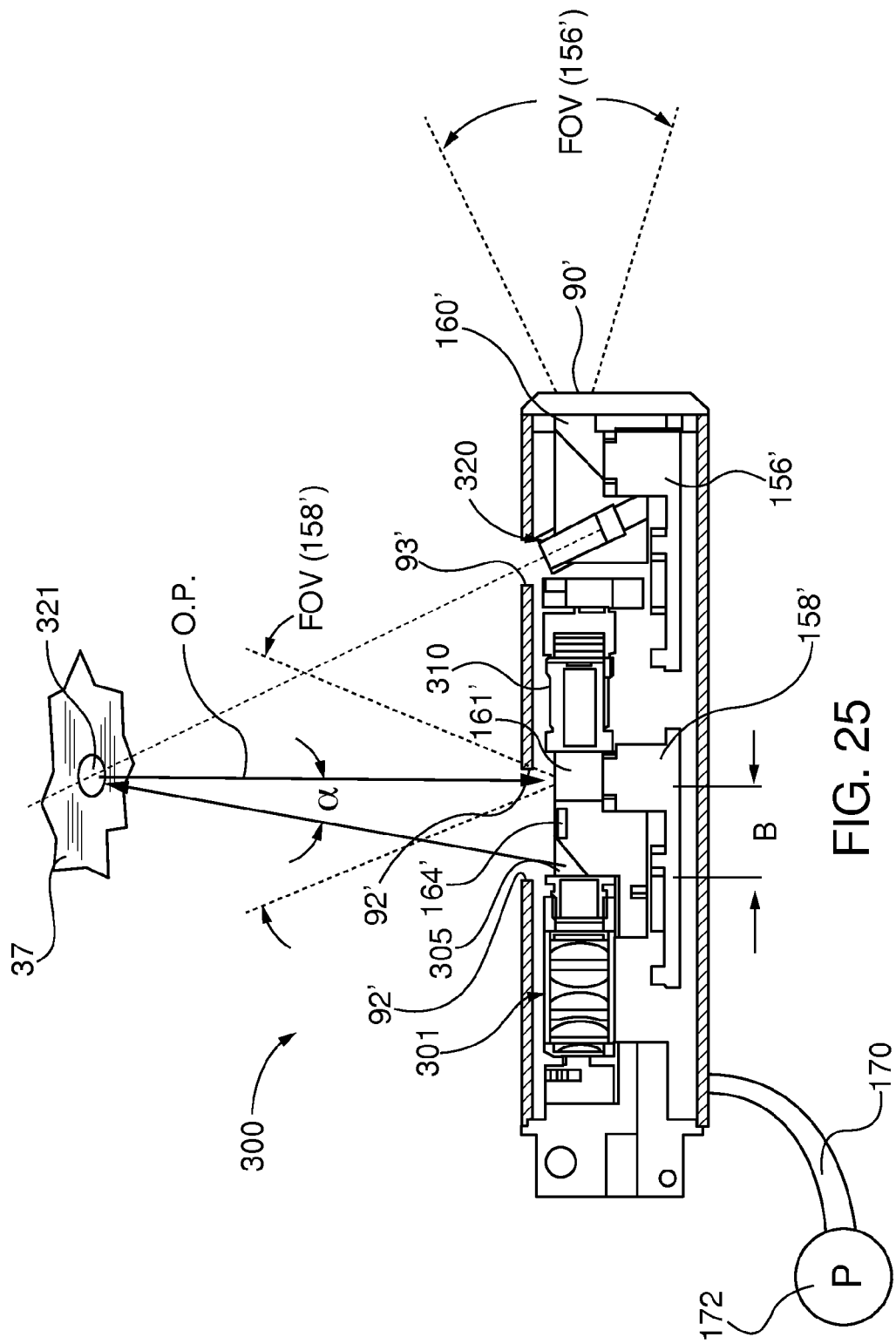
FIG. 25 is an partial axial cross-sectional schematic view of the camera head of the inspection system of FIG. 22.

Inspection scope 60, utilizing either of the camera head embodiments 66 or 66', is preferably externally cooled by a cooling air line 170 and pressurized cooling air source 172 (e.g., compressed air), schematically shown in the respective embodiments FIGS. 15 and 25. Cooling air passes through the scope 60 to transfer heat away from the instrument, where it exhausts through gaps within the scope outer surface, such as the camera ports 90, 92, 90', 92', the laser port 93', the prisms 160, 160', 164' around the cameras 156, 158, 156', 158', 310' and the LEDs 162, 164, 162', 164'. Those gaps effectively function as cooling air exhaust ports. Cooling air exhausting the various cooling ports helps transfer heat out of the scope 60 and helps create a thermal barrier around the camera head 88, 88' that is relatively cooler than the not fully cooled turbine 30 internal temperature. In this manner the inspection scope 60 can be inserted into still hot shut-down turbine many hours before it cools to ambient air temperature. In this manner inspection can be initiated many hours—and possibly days—earlier than was permissible with known inspection systems. Thus an inspection procedure can be initiated and completed earlier in a turbine service period than was possible in the past, possibly reducing the aggregate maintenance cycle time.

Camera Inspection Scope Control and Operation

Figure 16:
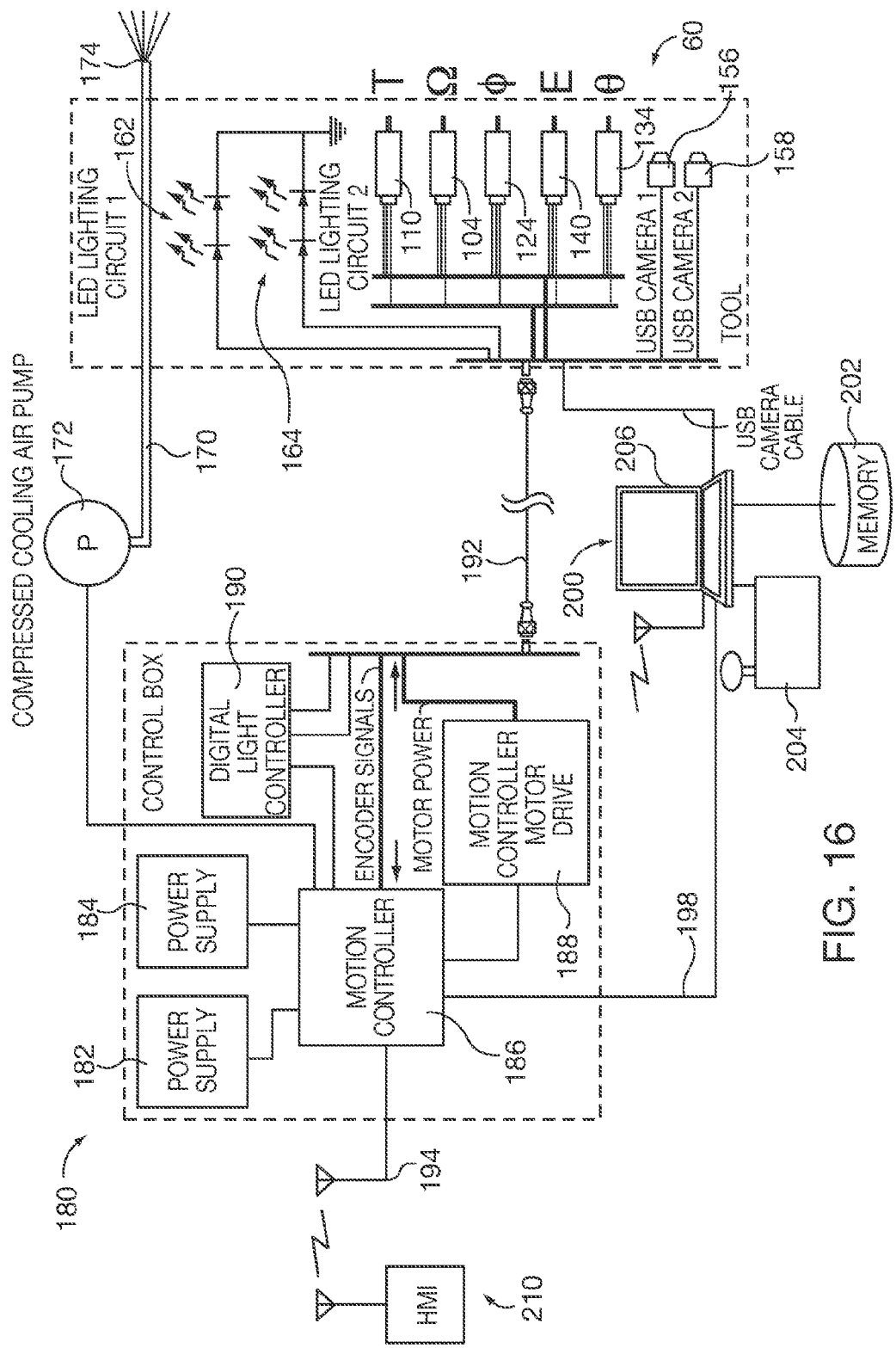
FIG. 16 is a block diagram of the control box and controls system for the optical camera inspection system of FIG. 5.
Figure 26:
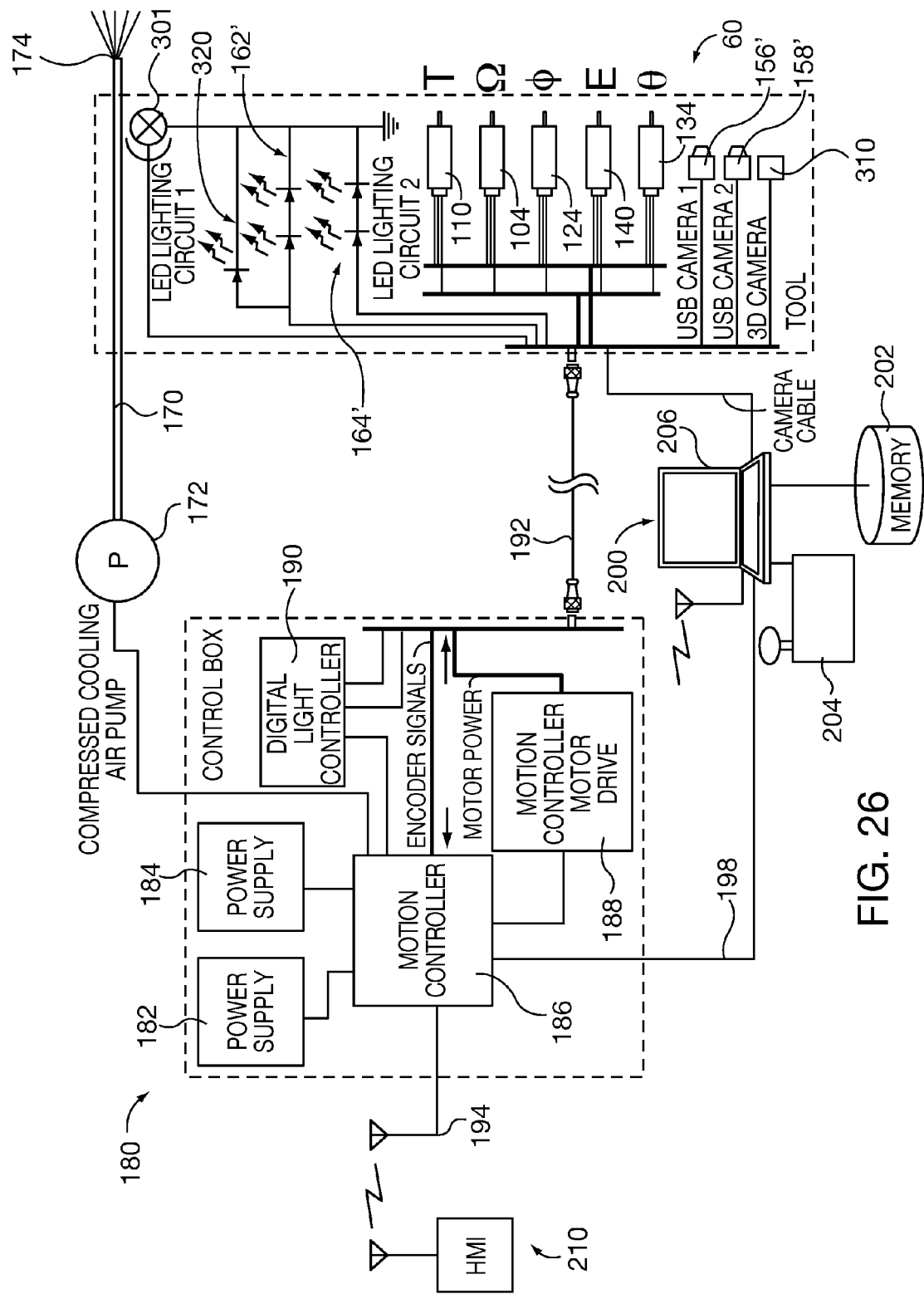
FIG. 26 is a block diagram of the control box and controls system for the optical camera inspection system of FIG. 22.

Inspection scope 60 positioning along its five degrees of motion are accomplished by energizing the five previously described precision motion control servo motors 104 (Ω), 110 (T), 124 (θ), 124 (Φ), and 140 (E). The servo motors have associated encoders that provide motor position information feedback for use by the controller of a known motion control system. FIG. 16 is block diagram of an exemplary motion control system of the present invention that is utilized with the camera head 66 of FIGS. 13-15. A corresponding block diagram for the camera head 66' of FIGS. 21-25 is shown in FIG. 26. In both FIGS. 16 and 26 common components and function are indicated with identical number and include the following common operational description. The previously described inspection scope 60 hardware are designated by dashed line 60, and is in communication with control box 180, also designated by dashed line, by way of known communication pathways, such as multi-pathway cable 192 and respective camera cables.

Control box 180 includes first and second power supplies 182, 184 for powering motion controller 186 and motion controller motor drive 188. All of components 182-188 are of known design utilized for industrial motion control systems. The motion controller 186 issues commands to the motion controller motor drive 188 for energizing and reversing the inspection scope 60 servo motors 104 (Ω), 110 (T), 124 (θ), 124 (Φ), and 140 (E). For brevity all such motors are collectively referred to as "servo motors". The respective servo motors have associated encoders that generate encoder signals indicative of the scope position within its respective range of motion. For example, the encoder associated with servo motor 104 generates a rotational position signal indicative of the gross rotational position (Ω) of the extension tube portion 62. Position signal information from each encoder is accessed by the motion controller 186. The motion controller 186 correlates respective motor encoder signals with inspection scope 60 spatial position. Digital light controller 190 controls the LEDs 162, 164 or 162', 164', luminal output and on/off (including strobe function, where applicable), the 3D scanning system 300 stripe projector 310 and the focus spot generating laser 320. The digital light controller 190 also communicates with the motion controller 186 and the host controller 200. The motion controller 186 also controls cooling air flow into and through the inspection scope 60, for example flow rate out the cooling port 174.

Motion controller 186 has an optional wireless communication capability 194. Hardwired data pathway 198, for example a cable transmitting communications signals in conformity with Ethernet protocol, is in communication with a host controller 200. An exemplary host controller 200 is a personal computer with internal memory capacity and if desired external memory 202. The host controller computer 200 also receives and processes image data from camera 156/156' (USB Camera 1), camera 158/158' (USB Camera 2) and 3D scanning system camera 310. The image data of the 3D scanning system camera 310 are processed to generate dimensional data respecting the scanned surface, such as that of the transition 37 of FIGS. 4 and 21 using known image processing software. An exemplary 3D scanning image processing software is the "MeshLab" package of open source software that is downloadable via the Internet from the National Research Council of Italy Visual Computing Lab. Another source for exemplary 3D scanning image processing software is Geomagic of Research Triangle Park, N.C., U.S.A. The host controller computer 200 may archive or otherwise store raw or processed image data in memory 202. Inspection scope 60 can be positioned under human command and control, such as via joystick 204 and/or HMI viewing/touch screen 206. Respective visual and reconstructed dimensional images from the cameras 156/156', 158/158' and 310 can be viewed by HMI viewing screen 206 or communicated to other image viewing or data processing systems via known communication pathways.

Figure 17:
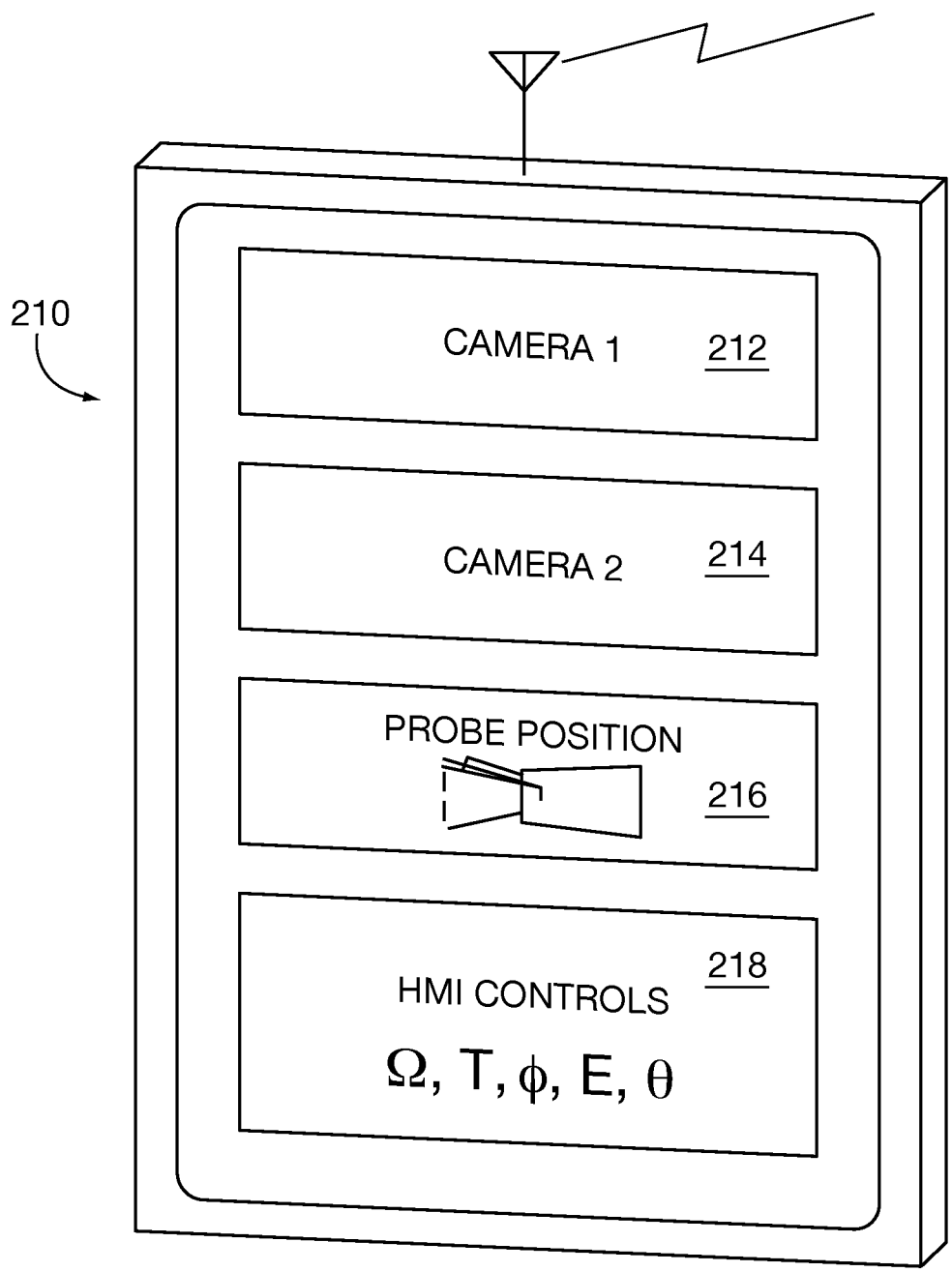
FIG. 17 is a perspective schematic view of an embodiment of a tablet computer human machine interface (HMI) for operator remote monitoring and control of an inspection system described in the present application.

Optionally the computer 200 may have wireless communication capability, for example to communicate with other computers, including for example a tablet computer 210 with HMI, such as for example a tablet computer. FIG. 17 shows an exemplary tablet computer HMI display screen including Camera 1 image display 212, Camera 2 image display 214, probe position information display 216 and an HMI control interface 218 for manipulating inspection scope 60 positions. The tablet computer 210 may have direct communications capability with the motion controller 186, without the need to communicate through the host controller computer 200.

Blade/Vane Inspection Scope

Figure 18:
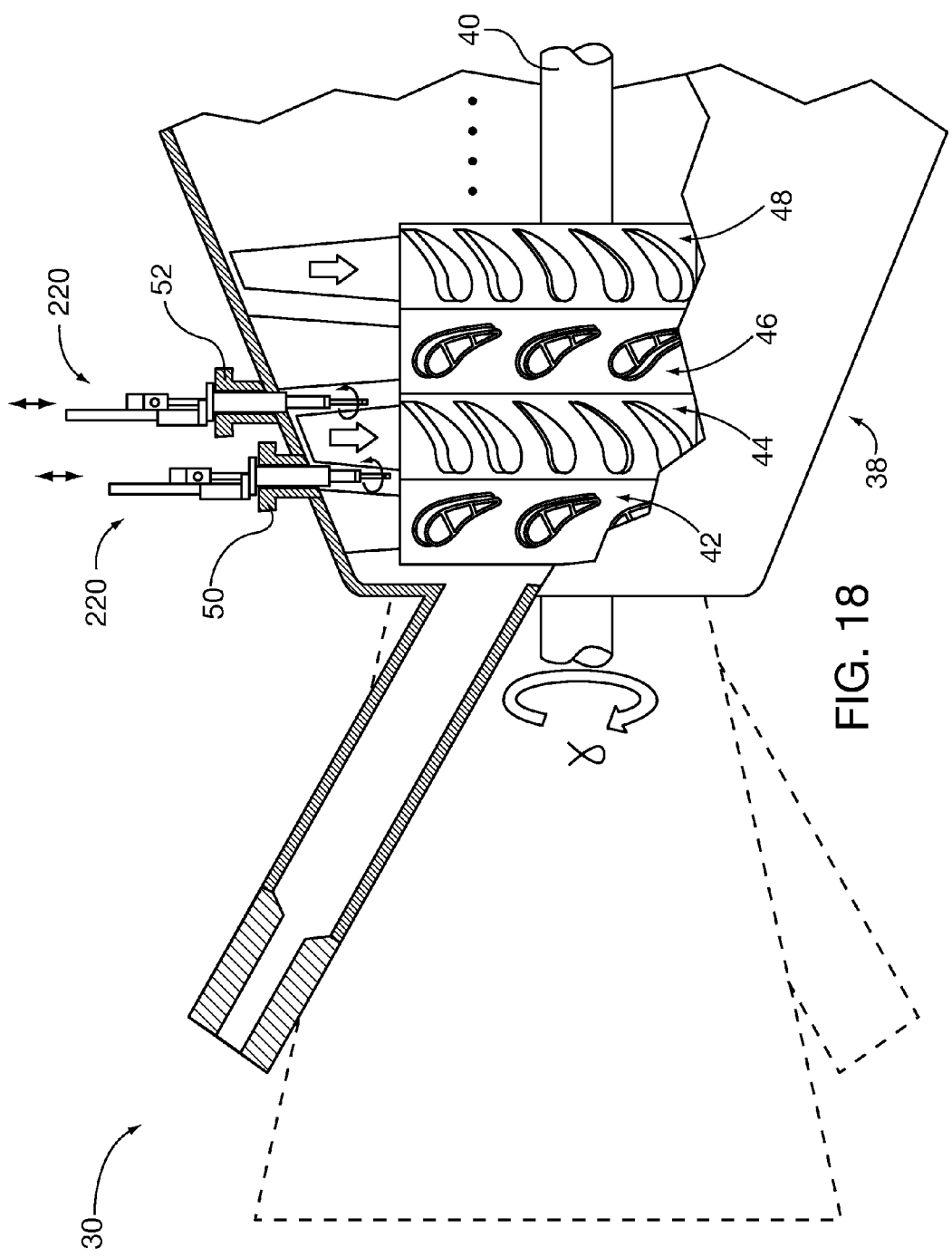
FIG. 18 is a partial cross sectional schematic view of a known gas turbine showing insertion of another optical camera inspection system described in the present application into two separate turbine section rows respective inspection ports.
Figure 19:
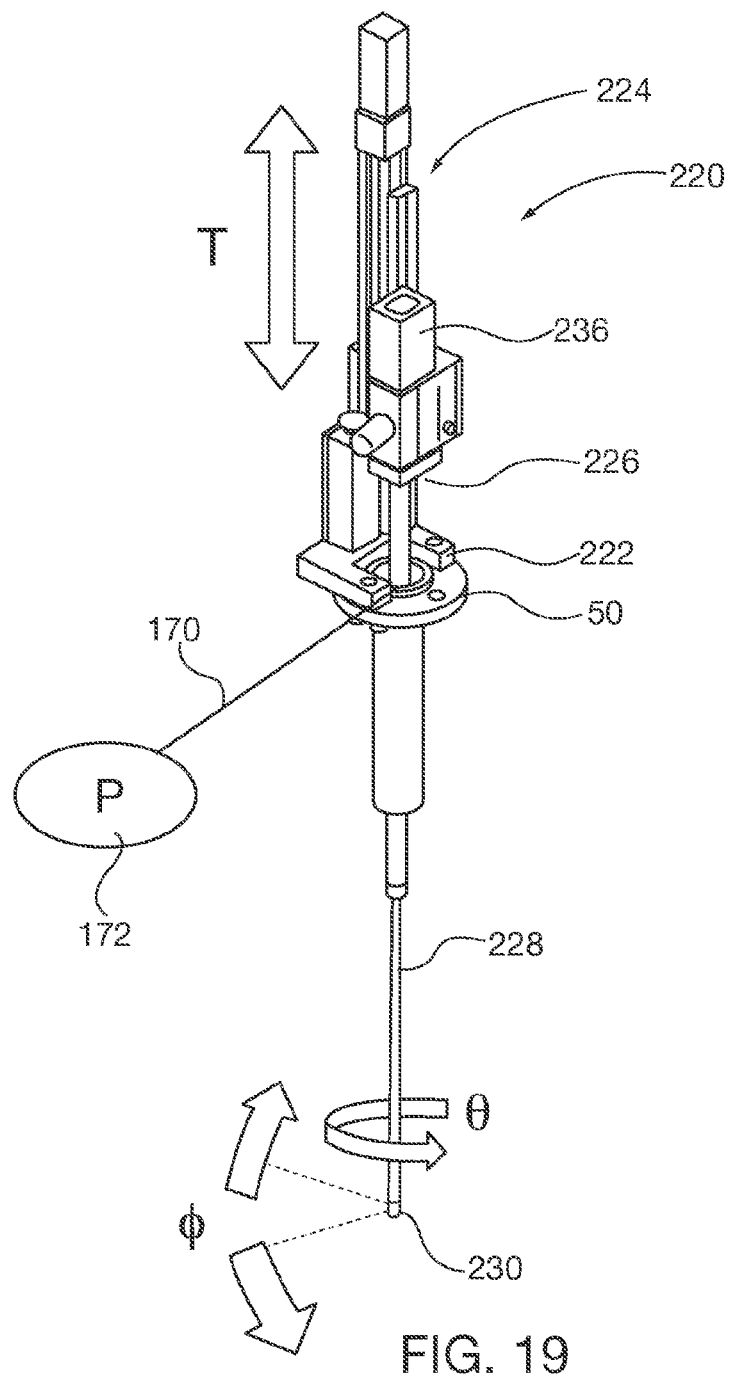
FIG. 19 is an elevational perspective view of optical camera inspection system embodiment of FIG. 18, showing available degrees of motion T, θ and Φ.
Figure 20:
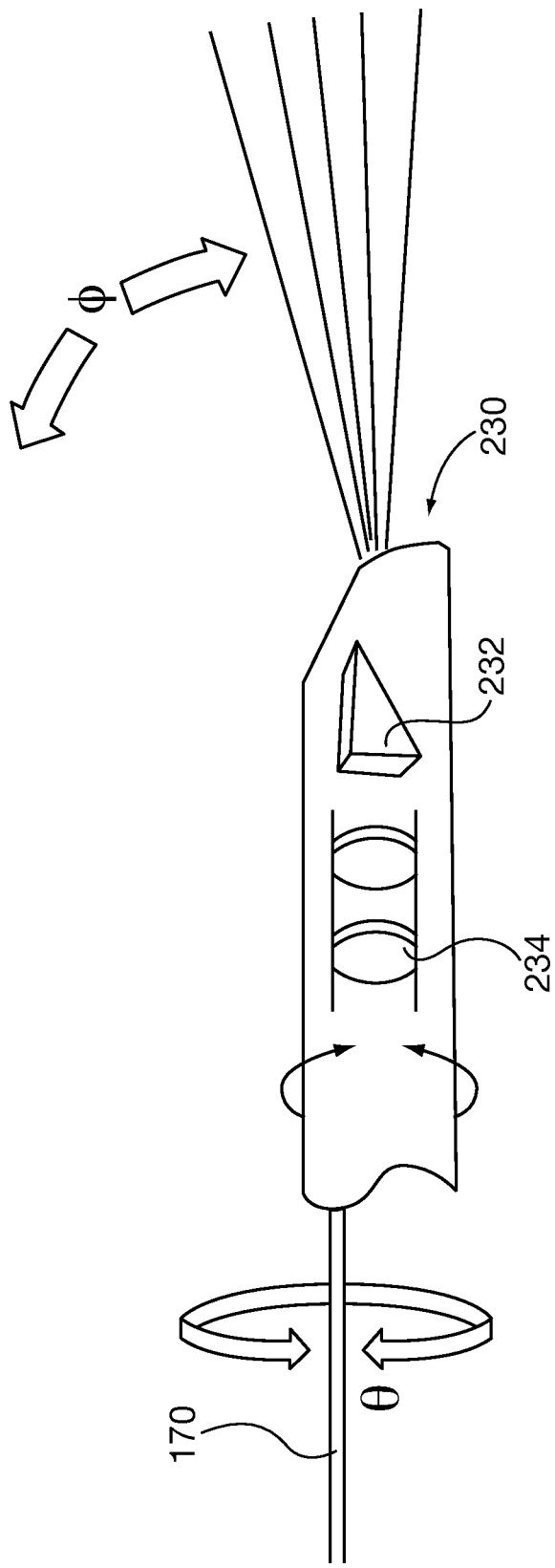
FIG. 20 is an elevational view of the swing prism articulation mechanism for the Φ degree of motion for the inspection system of FIG. 18.

A blade/vane inspection scope 220 embodiment is shown in FIGS. 18-20. This embodiment is particularly suitable for inspection within the confines of a gas turbine 30 turbine section 38, between rows of rotating blades and stationary vanes. FIG. 18 shows a pair of inspection scopes 220 respectively mounted to each of the Row 1 inspection port 50 and Row 2 inspection port 52. However, at the discretion of an inspection team a single inspection scope 220 may be mounted to a selected inspection port or more than two inspection scopes 220 may be mounted to the turbine 30 simultaneously during an inspection procedure. Similarly, an inspection team at its discretion may also operate one or more of the inspection scope 60 embodiments simultaneously with or without the inspection scope 220 embodiment in any inspection procedure.

As shown in FIGS. 19 and 20 the inspection scope 220 embodiment is mounted to a gas turbine inspection port (here a Row 1 inspection port 50) by mounting flange 222. Linear drive 224 with an associated servo motor and encoder translates the inspection scope in the telescoping extension position motion degree T. Rotational drive 226 with an associated servo motor and encoder rotates the inspection scope in the camera rotate/pan motion degree θ. Bore scope 228 is mechanically coupled to the linear drive 224 and rotational drive 226, and has a camera head 230 that captures within its field of view (FOV). The camera head 230 includes a pivoting prism 232 whose motion in the articulation Φ motion degree is imparted by an associated servo motor and encoder. The bore scope 228 is of known construction and includes fiber optic lenses 234 and auxiliary external lighting (not shown) that illuminate and transmit images within the camera head field of view to camera 236. The camera 236 may be an auto focusing USB camera that is coupled to a motion control system, such as shown in FIG. 16. General motion control and positioning of the inspection scope 220 along its motion degrees Φ, θ and T and camera image capture are performed as previously described with respect to the inspection scope embodiment 50.

The inspection scope 220 includes an external cooling system for inspection within a turbine 30 cool-down phase when the turbine section 30 still has an elevated temperature of up to approximately 150° C. As was described with respect to the inspection scope embodiment 50, the cooling system includes an air line 170 running in parallel to or within the bore scope 228 that expels cooling air obtained from a cooling air source through one or more functional cooling air exhaust ports, such as around the camera head 230.

The three motion degrees Φ, θ and T in the blade/vane inspection scope 220 embodiment are sufficient to obtain complete images of the leading or trailing sides of all rotating turbine blades within a given row while the turbine rotor is spinning in turning gear mode. For example in FIG. 18 the leading side of each of the Row 1 turbine blades 44 can be inspected by the inspection scope 220 that is positioned in inspection port 50. As each individual blade rotates within the camera head 230 field of view its image is captured by the associated control system. A partial or full series of blade images can be obtained during a single rotor 40 rotation while the turbine 30 is in turning gear mode. A single camera head 230 field of view may not capture the full radial length an area of interest on a turbine blade. By repositioning the camera head tilt angle Φ or inserting/retracting the bore scope 228 along the T freedom degree the camera field of view can be repositioned radially along the blade or vane length. Images captured at different blade/vane radial positions can be combined to create an aggregate image of the entire blade. Similarly, an image of the trailing edge of each blade 44 in Row 1 can be captured by positioning an inspection scope 220 in turbine inspection port 52, as was done for the leading edges.

Exemplary Turbine Inspection Procedures

The camera inspection system of the present invention provides the capability of automatic positioning and image capture of an inspection camera field of view relative to an area of interest with a turbine, such as a gas turbine, without human intervention. After inspection scope positioning sequence information is provided to the system, subsequent inspections are repeatable by different inspection teams, regardless of their individual inspection scope positioning skill or inspection speed. Automated inspections can be completed quicker, with less likelihood of human-created errors, as compared to known inspection procedures. Further explanation of the inspection methods of the present invention will be with reference to inspection of an exemplary industrial gas turbine.

Inspection scope positioning sequence information may be obtained by installing an inspection scope embodiment of the present invention on a selected inspection port and orienting all controlled motions to an initialized or "start" position. A human inspector guides the inspection scope through the control system HMI, e.g., by use of a joystick or touch screen pad, through a navigated path within the turbine that is recorded within one or both the control system controllers/host computer. The navigation path is chosen to orient the inspection scope camera head field of view within area of interest without causing undesirable impact of the scope with turbine internal components.

The control system retains the navigation path information from the initial human-controlled inspection and can subsequently repeat the inspection scope positioning sequence for future inspection cycles on the same turbine or other turbines having the same internal structure. For example, a navigation path sequence can be performed on a single test turbine and the sequence can be communicated to other remote sites for use by inspection teams inspecting the same structure gas turbine located at that site. In the field, an inspection team may be concerned that a different gas turbine may have variations in internal structure from the original gas turbine. The field team may review the stored navigation path individual step by step, with local override to accommodate any path variations needed for the field installation turbine to perform an inspection, or may choose to program a new navigation path dedicated to the field location turbine.

Navigation paths alternatively can be determined in virtual space by a human inspector simulating a navigation path in a simulated turbine and recording the path for subsequent use in actual turbine inspections. As another alternative, a scope inspection simulation program can prepare a suggested inspection navigation path for review and approval by a human inspector.

An automatically or manually controlled navigation path sequence can move the 3D scanning system camera head 66' field of view from one position of interest to another position of interest. For example, as shown in FIG. 4, an inspection scope 60 can be affixed to a combustor nozzle port 36, whereupon the inspection system can capture and record visual images of internal components within the combustor and transition 37 with cameras 156' and/or 158', preferably in conjunction with illumination from the illumination system 162', 164'. Three-dimensional scan data can be acquired with the 3D scanning system 300 within the camera head 66' in the alternative to or in conjunction with visual image. Both visual image data and 3D scan data may be combined in composite images.

When in a navigation path position the camera head 66' may be repositioned to obtain image information from different camera fields of view from the same reference position: for example by inserting the camera head 66' axially to a desired reference position and then rotating/panning the camera head 360 degrees about the entire inner circumference of transition 37 or any desired circumferential segment thereof. The various visual and/or 3D scanning images taken from the same reference point can be combined to obtain a composite or "stitched" view of the structural elements, or to take a virtual "tour" of any or all portions of the turbine interior.

Rather than move the inspection scope camera head field of view from one position to another, it is also possible to move the turbine component areas of interest within the field of view of a stationary camera head. For example, an inspection scope inserted between blade and vane rows can capture an image of each blade rotating within the camera field of view, whether the turbine is in turning gear mode or whether an operator manually "bumps" each blade of a completely stopped turbine rotor sequentially in front of the camera head.

Although various embodiments, which incorporate the teachings of the present invention, have been shown and described in detail herein, those skilled in the art can readily devise many other varied embodiments that still incorporate these teachings. For example, "optical images" of turbine internal component can be obtained in the visible light spectrum or in the infrared spectrum. The inspection scope motion degrees do not have to be limited to those exemplary motions enabled by the servo motors 104 (Ω), 110 (T), 124 (θ), 124 (Φ), and 140 (E). Scope motion does not have to be imparted by servo motors, and can include known alternative pneumatic or other motion control systems.

What is claimed is:

1. A system for internal three-dimensional scanning inspection of a turbine, comprising:
a base for affixation to a turbine inspection port,
an inspection scope having an extendable elongated body defining a central axis, with a proximal end rotatively coupled to the base and a distal end for insertion within a turbine inspection port;
a camera housing defining a central axis, for insertion within a turbine inspection port, having:
a proximal end coupled to the inspection scope distal end, a distal end, and
a structured light 3D scanner having a stripe projector for projecting a band of photons on an inspection surface of interest within a turbine interior, and a matrix camera having an optical path for capturing images of reflected photons that were projected on the inspection surface.

2. The system of claim 1 the camera housing further comprising a laser for projecting a distance reference focus dot for the 3D scanner.

3. The system of claim 1, further comprising a control system coupled to the 3D scanner for automatically capturing camera images of a turbine internal surface of interest without human intervention.

4. The system of claim 1, further comprising:
a control system coupled to the inspection scope and 3D scanner, for automatically positioning the inspection scope and matrix camera optical path along a pre-designated navigation path within a turbine to an internal surface of interest and for capturing a matrix camera image thereof without human intervention.

5. The system of claim 4, further comprising:
a first articulation joint, coupled to the control system, having:
a first articulation joint proximal end rotatively coupled to the inspection scope distal end that is capable of selective rotation about the inspection scope body central axis, and
a first articulation joint distal end, coupled to the camera housing proximal end that is capable of radial displacement relative to the inspection scope body central axis.

6. The system of claim 1, further comprising:
a first articulation joint having:
a first articulation joint proximal end rotatively coupled to the inspection scope distal end that is capable of selective rotation about the inspection scope body central axis, and
a first articulation joint distal end, coupled to the camera housing proximal end that is capable of radial displacement relative to the inspection scope body central axis.

7. The system of claim 6, further comprising:
the inspection scope having an extension portion intermediate the proximal and distal ends;
a gross rotation drive for rotating the inspection scope about its central axis, coupled thereto;
a scope extension drive for translating the extension portion, coupled thereto;
a first articulation drive, for articulating the camera housing central axis relative to the inspection scope central axis, coupled to the articulation joint; and
a control system coupled to the gross rotation, scope extension and first articulation drives and the structured light 3D scanner, for positioning the inspection scope and matrix camera optical path along a navigation path within a turbine to an internal area of interest and for selectively capturing respective camera images thereof.

8. The system of claim 1, further comprising the camera housing further having an illumination source and a second camera capable of capturing images in a second camera optical path.

9. The system of claim 8, further comprising:
a beam splitter optically coupling the matrix and second cameras optical paths in a shared optical path that is generally laterally aligned with the camera housing central axis; and
a prism optically coupled to the projector for projecting photons along an optical path that is generally laterally aligned with the camera housing central axis.

10. The system of claim 9, further comprising a third camera capable of capturing images in a third camera optical path that is generally parallel with the camera housing central axis.

11. The system of claim 10, further comprising LED illumination sources respectively in the camera housing distal end and lateral circumference, for selectively illuminating the second and third camera optical paths.

12. The system of claim 11, further comprising:
a laser for projecting a distance reference focus dot for the 3D scanner; and
a control system coupled to the 3D scanner, the second and third cameras, the LED illumination sources and the laser for automatically capturing camera images of a turbine internal surface of interest without human intervention.

13. The system of claim 11, further comprising:
a laser for projecting a distance reference focus dot for the 3D scanner; and
a control system coupled to the inspection scope, the 3D scanner, the second and third cameras, the LED illumination sources and the laser for automatically positioning the inspection scope and respective camera optical paths along a pre-designated navigation path within a turbine to an internal surface of interest and for capturing camera images thereof without human intervention.

14. The system of claim 13, further comprising:
a first articulation joint, coupled to the control system, having:
a first articulation joint proximal end rotatively coupled to the inspection scope distal end that is capable of selective rotation about the inspection scope body central axis, and
a first articulation joint distal end, coupled to the camera housing proximal end that is capable of radial displacement relative to the inspection scope body central axis.

15. A system for internal three-dimensional scanning inspection of a turbine, comprising:
a base for affixation to a turbine inspection port;
an inspection scope having an extendable elongated body defining a central axis, with a proximal end coupled to the base and a distal end for insertion within a turbine inspection port;
a first articulation joint having:
a first articulation joint proximal end rotatively coupled to the inspection scope distal end that is capable of selective rotation about the inspection scope body central axis, and
a first articulation joint distal end that is capable of radial displacement relative to the inspection scope body central axis;
a camera housing defining a central axis, for insertion within a turbine inspection port, having
a proximal end coupled to the first articulation joint distal end,
a distal end, and
a structured light 3D scanner having a stripe projector for projecting a band of photons on an inspection surface of interest within a turbine interior, and a matrix camera having an optical path for capturing images of reflected photons that were projected on the inspection surface,
a first camera coupled to the camera housing, capable of capturing images in a first camera optical path that is generally parallel with the camera housing central axis, and
a second camera coupled to the camera housing, capable of capturing images in a second camera optical path that is generally laterally aligned with the camera housing central axis;
a first articulation drive, for articulating the camera housing central axis radially and parallel to the inspection scope central axis, coupled to the first articulation joint; and
a control system, coupled to the first articulation drive, the structured light 3D scanner and the first and second cameras, for positioning the inspection scope and respective camera optical paths along a navigation path within a turbine to an internal area of interest and for selectively capturing respective camera images thereof.

16. A method for performing internal dimensional measurement inspection of a turbine, comprising:
providing a three-dimensional (3D) scanning system having:
a base for affixation to a turbine inspection port,
an inspection scope having an extendable elongated body defining a central axis, with a proximal end rotatively coupled to the base and a distal end for insertion within a turbine inspection port;
a camera housing defining a central axis, for insertion within a turbine inspection port, having:
a proximal end coupled to the inspection scope distal end,
a structured light 3D scanner having a stripe projector for projecting a band of photons on an inspection surface of interest within a turbine interior, and a matrix camera having an optical path for capturing images of reflected photons that was projected on the inspection surface;
affixing the base to a turbine inspection port;
inserting the inspection scope and camera housing into the inspection port; inspecting the turbine by positioning the inspection scope and camera housing along a navigation path, projecting the band of photons on an inspection surface of interest, and capturing matrix camera images thereof; and
determining the inspected turbine's internal dimensional measurements with the matrix camera images.

17. The method of claim 16 further comprising:
providing a control system coupled to the inspection scope and camera housing for automatically positioning the inspection scope and matrix camera optical path along a pre-designated navigation path within the turbine and for capturing a matrix camera image thereof without human intervention;
providing the navigation path to the control system; and
inspecting the turbine by automatically positioning the inspection scope and matrix camera optical path along the navigation path with the control system and capturing a matrix camera image thereof without human intervention.

18. The method of claim 17 further comprising constructing a dimensioned virtual image of the inspected turbine with captured matrix camera images.

19. The method of claim 16 further comprising:
the camera housing further having an illumination source and a second camera capable of capturing images in a second optical path;
selectively activating the illumination source; and
capturing the second camera images.

20. The method of claim 19 further comprising:
- providing a control system coupled to the inspection scope and camera housing for automatically positioning the inspection scope and matrix camera optical path along a pre-designated navigation path within the turbine and for capturing a matrix camera images thereof without human intervention;
- providing the navigation path to the control system;
- inspecting the turbine by positioning the inspection scope and matrix camera optical path along the navigation path with the control system and capturing automatically without human intervention in any sequence matrix camera or second camera images or both types of images; and
- constructing a dimensioned virtual image of the inspected turbine with the captured images.

* * * * *